US012736492B2

(12) United States Patent
Seo

(10) Patent No.: US 12,736,492 B2
(45) Date of Patent: Sep. 15, 2026

(54) GAS SENSOR COMPRISING CARBON STRUCTURE HAVING HIGH ADSORPTION PERFORMANCE FOR GAS AND METHOD FOR MANUFACTURING THE SAME

(71) Applicant: Hongik University Industry-Academia Cooperation Foundation, Seoul (KR)

(72) Inventor: Jung Hwan Seo, Seoul (KR)

(73) Assignee: Hongik University Industry-Academia Cooperation Foundation, Seoul (KR)

( * ) Notice: Subject to any disclaimer, the term of this patent is extended or adjusted under 35 U.S.C. 154(b) by 337 days.

(21) Appl. No.: 18/429,849

(22) Filed: Feb. 1, 2024

(65) Prior Publication Data

US 2024/0255456 A1 Aug. 1, 2024

(30) Foreign Application Priority Data

Feb. 1, 2023 (KR) ........................ 10-2023-0013604

(51) Int. Cl.
*G01N 27/12* (2006.01)
*G01N 33/00* (2006.01)

(52) U.S. Cl.
CPC ....... *G01N 27/125* (2013.01); *G01N 33/0027* (2013.01)

(58) Field of Classification Search
CPC ............. G01N 27/125; G01N 33/0027; G01N 27/128; C01B 32/182; C01B 32/198; G03F 7/70383
USPC ........................................................ 73/31.06
See application file for complete search history.

(56) References Cited

U.S. PATENT DOCUMENTS

2015/0323482 A1* 11/2015 Shimoyama ....... G01N 27/4146 73/31.06
2017/0016867 A1* 1/2017 Chung ............... G01N 33/0036
2023/0193469 A1* 6/2023 Wable ................... C01B 32/154 427/554

FOREIGN PATENT DOCUMENTS

CN 108918597 A * 11/2018 .............. B01J 20/20
CN 115165977 B * 11/2024 ........... G01N 27/127
KR 1994-0015498 7/1994
KR 10-2012-0018684 A 3/2012
KR 10-2301531 9/2021
KR 10-2022-0001252 A 1/2022
KR 10-2022-0066833 A 5/2022
KR 10-2022-0073679 A 6/2022
(Continued)

OTHER PUBLICATIONS

Taejung Kim et al., "Development of a Novel Gas-Sensing Platform Based on a Network of Metal Oxide Nanowire Junctions Formed on a Suspended Carbon Nanomesh Backbone", Jul. 1, 2021, MDPI, Sensors 2021, 21,4525, pp. 1-13 (Year: 2021).*
(Continued)

*Primary Examiner* — Marrit Eyassu
(74) *Attorney, Agent, or Firm* — Fish & Richardson P.C.

(57) ABSTRACT

A method for manufacturing a gas sensor includes forming an electrode pattern; forming a carbide material layer on the electrode pattern; carbonizing, based on an irradiation of a laser on the carbide material layer, the carbide material layer to form a carbon structure capable of adsorbing gas particles; and electrically connecting a measurement device to the electrode pattern. The measurement device is configured to measure electrical properties of the electrode pattern. The gas sensor is capable of detecting hazardous materials such as nitrogen oxide.

16 Claims, 24 Drawing Sheets

(56) References Cited

FOREIGN PATENT DOCUMENTS

| | | | | | |
|---|---|---|---|---|---|
| KR | 20220073679 A | * | 6/2022 | ........... | G01N 27/125 |
| TW | 202138800 A | * | 10/2021 | | |

OTHER PUBLICATIONS

Kim et al., "Development of a Novel Gas-Sensing Platform Based on a Network of Metal Oxide Nanowire Junctions Formed on a Suspended Carbon Nanomesh Backbone," Sensors, Jul. 2021, 21(13):4525, 13 pages.

Office Action in Korean Appln. No. 10-2023-0013604, mailed on Sep. 3, 2024, 15 pages (with English translation).

Yang et al., "Intrinsically Breathable and Flexible $NO_2$ Gas Sensors Produced by Laser Direct Writing of Self-assembled Block Copolymers," ACS Applied Materials & Interfaces, Apr. 2022, 14(15):17818-17825.

* cited by examiner

GAS SENSOR COMPRISING CARBON STRUCTURE HAVING HIGH ADSORPTION PERFORMANCE FOR GAS AND METHOD FOR MANUFACTURING THE SAME

CROSS-REFERENCE TO RELATED APPLICATION

This application claims priority to Korean Patent Application No. 10-2023-0013604, filed on Feb. 1, 2023, and all the benefits accruing therefrom under 35 U.S.C. § 119, the contents of which in its entirety are herein incorporated by reference.

TECHNICAL FIELD

The present disclosure relates to a gas sensor and a method for manufacturing the same. More particularly, the present disclosure relates to a gas sensor that includes a carbon structure with high adsorption performance for gaseous phase materials having a wide range of vapor pressures.

BACKGROUND

When unexpected hazardous material spills in air occur in industrial environments, many types of safety accidents including human injuries may occur. The effects of hazardous materials on human health may vary depending on the type of the hazardous materials, and in some cases, they may produce adverse effects in a very short time. Accordingly, it is necessary to quickly detect the type and concentration of the hazardous materials contained in air to take appropriate measures.

A variety of sensor systems have been studied to detect hazardous materials in gases. For example, a sensor system can deliver gases into a sensor using the power of a pump for a predetermined time and measure changes in electrical/chemical reaction with the sensor surface, and another method can place a sensor in air or ambient surroundings and measure reaction with a sensing unit of the sensor through a spontaneous diffusion process of gases.

For example, the sensor can include a pump cell configured to produce an oxygen carrier and having a pump electrode disposed on a support for a solid electrolyte in order to measure the components of gases in a gas mixture and the concentration of the gases. However, high power is required due to the pump being used to introduce gases into the sensor. The gas detection using the sensor in the air requires a considerable amount of time to analyze hazardous materials since it is not easy to introduce outdoor gases into the sensing unit of the sensor. Accordingly, it may be difficult to properly use in industrial sites where immediate measures must be taken in the event of hazardous gas spills. Furthermore, since the conventional sensor systems can require many additional components such as pumps, etc., they have sophisticated architecture and a large size, which place limitations on the use of a wide range of applications over the entire area of the industrial sites.

On the other hand, graphene is a naturally abundant and low-cost carbon-based material, and possesses high electron mobility, mechanical strength and thermal conductivity and has alignment and large-scale application advantages over carbon nanotubes or nanowires. Accordingly, studies have been made to manufacture gas sensors for detecting hazardous materials using the characteristics of graphene.

However, conventional graphene-based gas sensors are manufactured by ion beam irradiation on a portion of graphene for adsorption of gas particles on the graphene and plasma treatment of the other portion before or after the ion beam irradiation. This technology has a complex manufacturing process and needs many types of equipment to manufacture, and thus cannot be easily applied in industrial sites. Additionally, the graphene-based gas sensors do not consider the gas desorption mechanism and cannot achieve sensors with repeatability or reproducibility.

SUMMARY

According to the present disclosure, systems and methods are provided for manufacturing a gas sensor having a carbon structure that changes electrical properties when it contacts gas molecules. One of the methods can include forming a carbide material that includes a photoresist on an electrode pattern and carbonizing the carbide material by a carbon dioxide ($CO_2$) laser, a gas sensor including the carbon structure and an operation method thereof.

A method for manufacturing a gas sensor includes forming an electrode pattern; forming a carbide material layer on the electrode pattern; carbonizing, based on an irradiation of a laser on the carbide material layer, the carbide material layer to form a carbon structure capable of adsorbing gas particles; and electrically connecting a measurement device to the electrode pattern. The measurement device can be configured to, based on the carbon structure being exposed to the gas particles, measure electrical properties of the electrode pattern.

In some implementations, the carbide material layer includes SU-8.

In some implementations, forming the carbon structure includes carbonizing the carbide material layer by irradiating a carbon dioxide ($CO_2$) laser onto the carbide material layer.

In some implementations, carbonizing the carbide material layer can include moving a laser oscillator configured to emit the $CO_2$ laser at a preset speed on the carbide material layer and adjusting at least one of the preset speed, an amount of the laser irradiation, or an output of the laser oscillator to form the carbon structure having a planar or 3-dimensional arrangement.

In some implementations, the carbide material layer can include a photoresist, and forming the carbide material layer can include mixing a photoresist solution with an ethanol solution and applying a mixed solution onto the substrate.

In some implementations, the applying the mixed solution onto the substrate can include adjusting a viscosity of the mixed solution of the photoresist solution and the ethanol solution to form the carbide material layer with a preset thickness.

In some implementations, the ethanol solution can include a bonding material that is dispersed in the ethanol solution and capable of selectively adsorbing the gas particles.

In some implementations, the method for manufacturing the gas sensor can further include, after forming the carbon structure, forming a bonding material layer capable of selectively adsorbing the gas particles on the carbon structure.

In some implementations, forming the bonding material layer can include applying an ethanol solution in which quantum dots including a metal oxide are dispersed onto the carbon structure and evaporating the ethanol solution applied on the carbon structure.

A gas sensor according to an aspect of the present disclosure includes an electrode pattern; a carbon structure located on the electrode pattern and having pores for adsorption of gas particles; and a measurement device electrically connected to the electrode pattern and configured to detect the gas particles by measuring a change in electrical properties of the electrode pattern when the carbon structure is exposed to the gas particles.

In some implementations, the carbon structure can be formed by carbonization of a material including carbon and includes a planar or 3-dimensional arrangement of at least one of a carbon compound, graphene, or graphene oxide.

In some implementations, the gas sensor can include a bonding material layer that is located on the carbon structure and capable of selectively adsorbing the gas particles.

In some implementations, the bonding material layer can include metal oxide quantum dots.

A method of operating a gas sensor includes exposing a carbon structure located on an electrode pattern and having pores for adsorption of gas particles to gaseous phase materials including the gas particles for a first preset time; and measuring electrical properties of the electrode pattern after the exposure to the gaseous phase materials.

In some implementations, the method can include: interrupting a supply of the gaseous phase materials to the carbon structure for a second preset time to recover the electrical properties of the electrode pattern; and heating the carbon structure at a preset temperature.

In some implementations, exposing the carbon structure to the gaseous phase materials and interrupting the supply of the gaseous phase materials are repeatedly performed.

In some implementations, the method can include: adjusting at least one of the preset temperature, a length of the first preset time, or a length of the second preset time such that a difference between (i) the electrical properties of the electrode pattern after interrupting the supply of the gaseous phase materials and (ii) the electrical properties of the electrode pattern before exposing to the gaseous phase materials is less than a preset threshold.

A method for manufacturing the gas sensor includes forming the carbide material that includes the photoresist on the electrode pattern and carbonizing the carbide material by $CO_2$ laser, thereby forming the carbon structure capable of adsorbing gas particles through the fine bonding structure of carbon similar to graphene and having the outstanding properties such as the surface-area-to-volume ratio, thermal conductivity, electrical conductivity, and ion diffusivity.

The carbon structure of the gas sensor manufactured according to an aspect of the present disclosure has high specific surface area and high adsorption performance for gaseous phase materials having a wide range of vapor pressures from low vapor pressure to high vapor pressure.

When the carbon structure is exposed to gas particles such as hazardous materials, the gas particles can be adsorbed onto the lattice defects, i.e., the pores of the carbon structure, causing a change in electrical properties (for example, resistance) of the carbon structure, and thus it may be possible to achieve the gas sensor that detects the hazardous materials through the resistance change of the electric circuit including the electrode pattern connected to the carbon structure.

The gas sensor according to an aspect of the present disclosure can be manufactured through the simple process of carbonizing the carbide material layer on the electrode pattern by the laser, so it is easier to manufacture than the conventional gas sensor. Additionally, since the carbon structure is kept in the heated state for the predetermined time after the gas supply is interrupted, it may be possible to desorb the adsorbed gas particles from the carbon structure and recover the initial properties of the gas sensor, thereby performing the sensing operation with repeatability and reproducibility.

DETAILED DESCRIPTION

Figure 1:
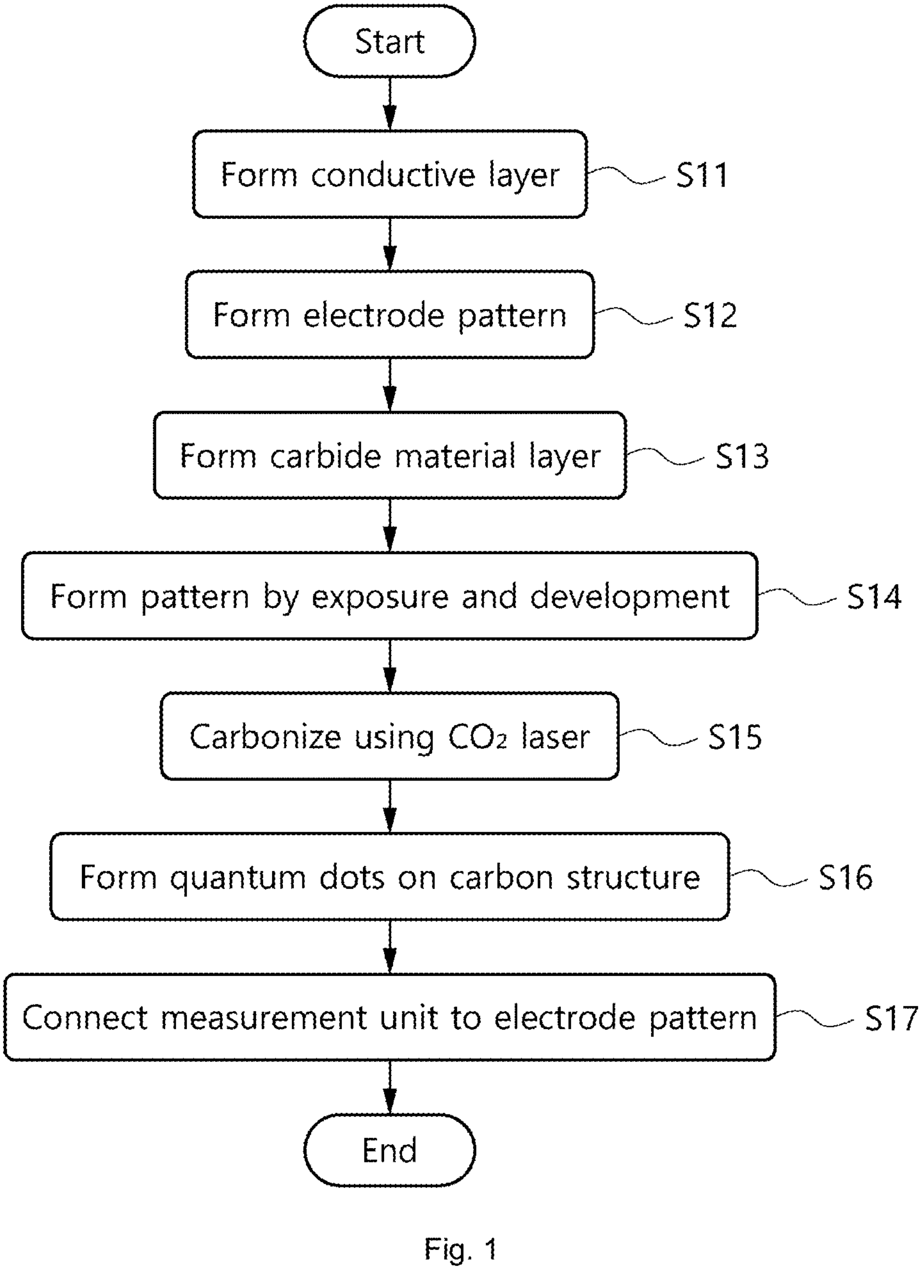
FIG. 1 is a flowchart illustrating an example of a method for manufacturing a gas sensor.

Hereinafter, example implementations of the present disclosure will be described with reference to the accompanying drawings. The present disclosure is described with reference to the implementations shown in the drawings, but the description is provided as an implementation and the technical spirit of the present disclosure and its essential components and operation are not limited thereto.

Although currently widely used general terms have been selected and used herein, considering the function in the present disclosure, this may vary depending on the intention or practice of a skilled person in the art, the emergence of new technologies, or the like. In addition, in certain cases, there are some terms selected by the applicant, and in this case, the meanings thereof will be described in detail in the corresponding description of the present disclosure. Therefore, the terms used herein should be defined based on the meanings of the terms and throughout the content of the present disclosure, not just on the names of the terms.

When a part "includes" a component as described in the entire specification, it means that the part may further include other components without excluding other components unless otherwise stated. In addition, when a part is "connected" with other part as described in the specification, it means that the part is "connected directly" with other part, or connected with other part "with a further part interposed therebetween".

Hereinbelow, implementations of the present disclosure will be described in detail so that the implementations can be easily implemented by a person having ordinary skill in the art to which the present disclosure pertains. However, the present disclosure is not limited to the disclosed implementations, but may be implemented into various different forms. In addition, in order to clearly describe the present disclosure in the drawings, elements that are not relevant to the corresponding description were omitted, and like elements are denoted as like reference numbers throughout the specification.

The present disclosure will be described in detail with reference to the accompanying drawings.

FIG. 1 is a flowchart illustrating an example of a method for manufacturing a gas sensor. FIGS. 2A to 2G are perspective views illustrating an example of a process state for each step of a method for manufacturing the gas sensor.

Figure 2A:
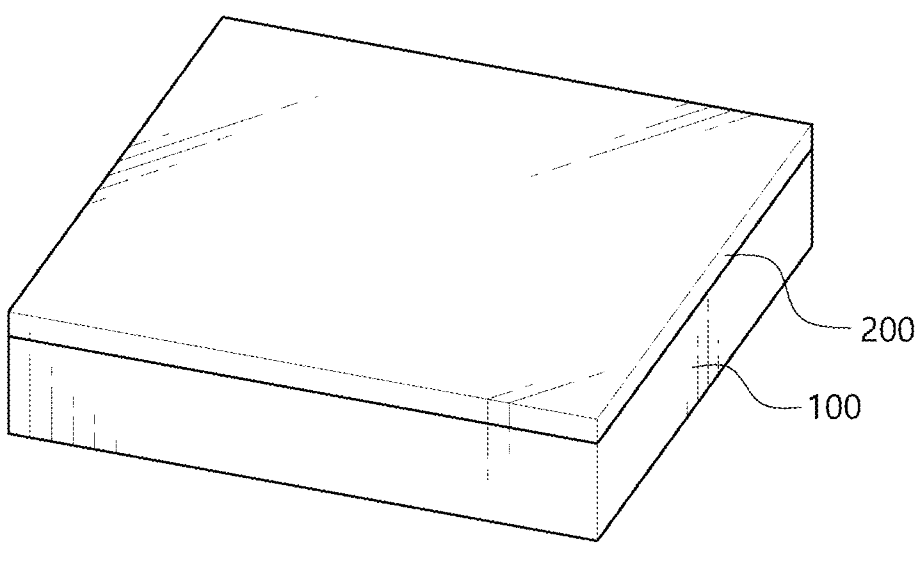
FIGS. 2A to 2G are perspective views illustrating an example of a process state for each step of a method for manufacturing a gas sensor.

Referring to FIGS. 1 and 2A, to manufacture the gas sensor, first, a conductive layer 200 may be formed on a substrate 100 (S11). In the present disclosure, the substrate 100 may act as a support for the fabrication of the gas sensor, and for example, may be a silicon or Silicon on Insulator (SOI) wafer, etc., but is not limited thereto. The substrate 100 for manufacturing a sensor element is well known to those skilled in the art, and its detailed description is omitted.

The conductive layer 200 is a portion to be patterned into an electrode, and may be made of metal such as titanium (Ti), platinum (Pt) or other conductive material, and may be formed from an alloy including a combination thereof or other material.

Figure 2B:
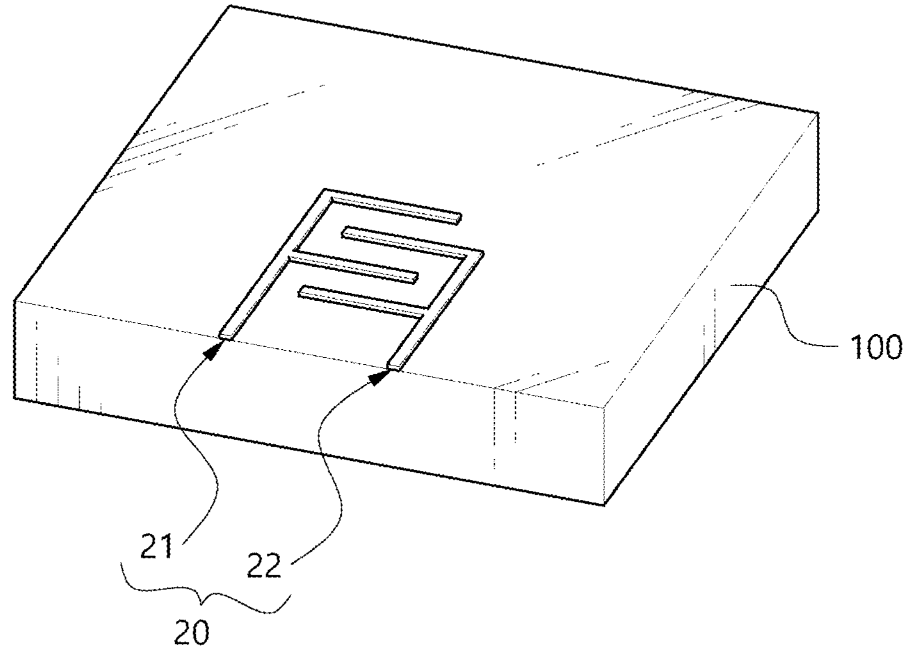
Figure 2C:
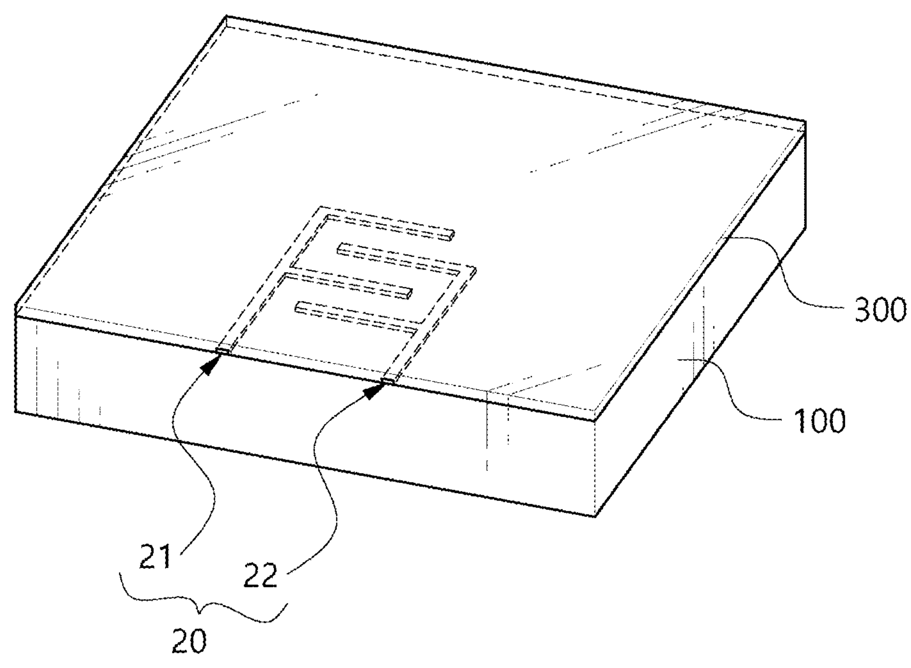

Subsequently, referring to FIG. 2B, an electrode pattern 20 may be formed by patterning the conductive layer 200 into a preset shape (S12). The electrode pattern 20 may be formed by a known patterning method such as photolithography including forming a photoresist, patterning by a mask and removing the exposed portion of the conductive layer by etching or any patterning method that will be developed, and this is well known in the technical field pertaining to the present disclosure and its detailed description is omitted.

In some implementations, the electrode pattern 20 has a pair of comb structures 21, 22 engaged with each other into an electrode shape. After a process of preparing a carbon structure as described below, gas particles may be detected through resistance changes between the comb structures 21, 22. However, the electrode pattern 20 may be patterned in other shape, and is not limited by the shape shown in the drawings of the present disclosure.

Subsequently, a carbide material layer 300 may be formed on the substrate 100 having the electrode pattern 20 (S13). The carbide material layer 300 is where the carbon structure will be formed by patterning and laser-assisted carbonization through the following steps. The carbide material layer 300 may be made of polymer that may be carbonized when energy, for example, a laser is applied due to including carbon. In some implementations, the carbide material layer 300 can include a photoresist which is a polymer that selectively changes in solubility as it is crosslinked or changes in chemical structure in response to light or any other material.

In some implementations, the carbide material layer 300 can include SU-8, i.e., a negative photoresist that is sensitive to ultraviolet light. In this implementation, SU-8 is used as a precursor for carbon in the fabrication of a carbon-based microstructure, and the carbon structure having similar characteristics to graphene may be formed by carbonizing the SU-8 based photoresist as described below. However, in the method for manufacturing the gas sensor according to implementations, the material of the carbide material layer 300 is not limited thereto, and the carbide material layer 300 may be made of any other material that may be carbonized using lasers.

The carbide material layer 300 may be applied onto the substrate 100 in a liquid phase including the photoresist such as SU-8. For example, a photoresist solution may be prepared by dissolving the SU-8 photoresist and a photoinitiator (PI) (for example, IRGACURE 261, etc.) that causes polymerization reaction by ultraviolet light in a predetermined solvent (for example, gamma-butyrolactone (GBL), etc.), but is not limited thereto. Additionally, in some implementations, an adhesive layer may be additionally formed between the substrate 100 and the carbide material layer 300.

In some implementations, the carbide material layer 300 may be formed by applying a mixed solution of the photoresist solution and ethanol onto the substrate 100. In this mixed solution, the ethanol plays a role in lowering the viscosity of the photoresist solution, and for example, a photoresist layer 200 may be formed with a smaller thickness by adjusting the viscosity of the photoresist solution to form the carbide material layer 300 of a desired thickness. When the thickness of the carbide material layer 300 is small, the adsorption characteristics of gas particles on the surface of the carbon structure to be formed may be improved, and thus the use of the mixture of the photoresist solution and the ethanol at an optimal ratio may improve the sensitivity of the gas sensor.

The carbide material layer 300 is formed on the substrate 100 to cover at least a region at which the electrode pattern 20 is located. In some implementations, the carbide material layer 300 may be formed on the front surface of the substrate 100 and patterned through exposure and development processes to form a pattern 30 of carbide material (S14). For example, the carbide material pattern 30 may be formed by photolithography.

Figure 2D:
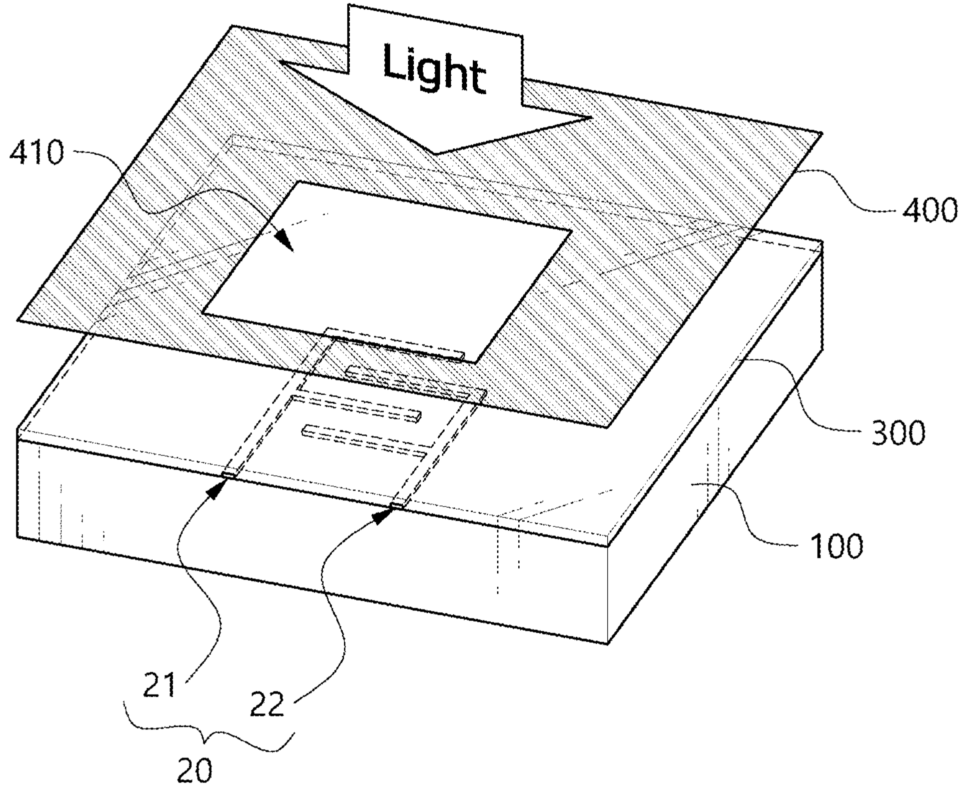

First, as shown in FIG. 2D, a mask layer 400 configured to block light may be disposed on the carbide material layer 300. In this instance, the mask layer 400 has an opening 410 corresponding to the pattern to be formed, and when the mask layer 400 is illuminated with light from top, the carbide material layer 300 below the opening 410 is exposed to light and polymerization reaction occurs.

In some implementations, since the SU-8 in the carbide material layer 300 has negative photosensitive properties, the portion below the opening 410 exposed to light becomes insoluble in a developer solution. In this instance, the light used may be ultraviolet light of about 300 to 400 nm wavelengths or visible light of about 400 to 450 nm wavelengths, but is not limited thereto, and the characteristics of light may vary depending on the material of the carbide material layer 300.

Figure 2E:
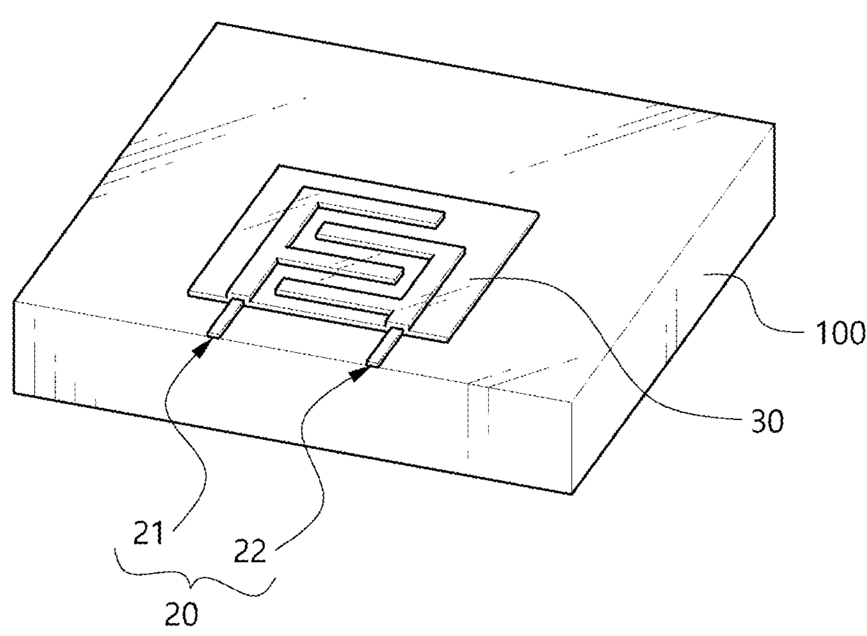

When the carbide material layer 300 having undergone the exposure is exposed to the developer solution, as shown in FIG. 2E, the carbide material pattern 30 corresponding to the exposed portion may be formed and the carbide material of the remaining portion may be removed. In this instance, the developer solution may include propylene glycol mono methyl ether (PGMEA), 1-Methoxy-2-propanol acetate, etc. to remove the SU-8, but is not limited thereto.

The carbide material pattern 30 formed by the aforementioned process has a shape corresponding to the mask (the opening 410 in FIG. 2D) used in the exposure process. However, in other implementation, the photoresist may be other material having positive photosensitive properties, and in this case, the portion in which light is blocked by the mask may be formed as the carbide material pattern 30.

Figure 2F:
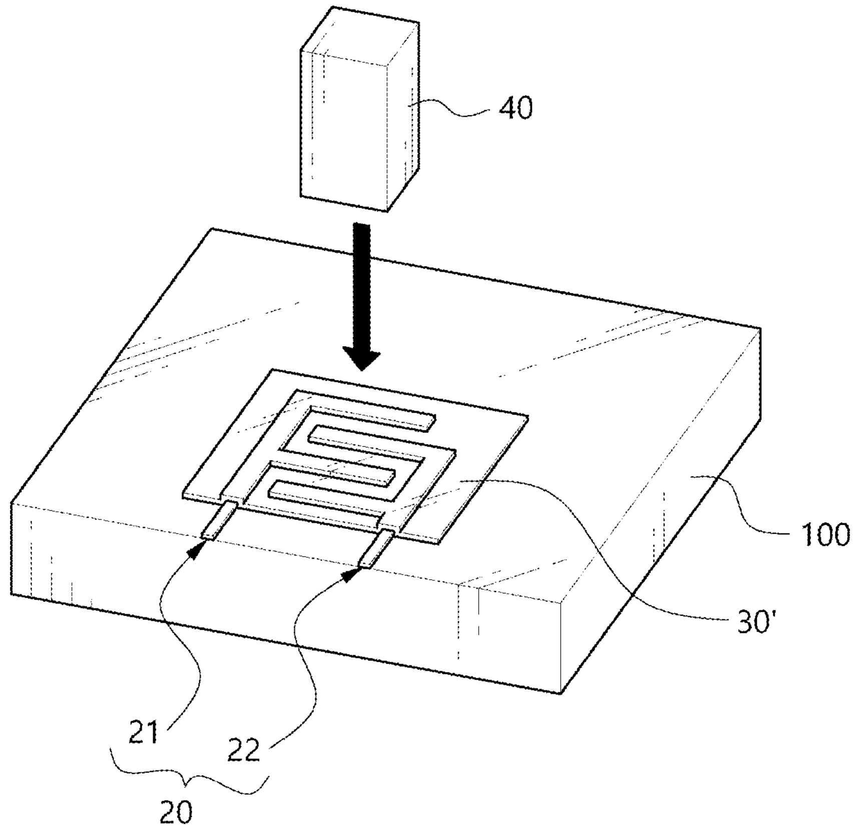

Subsequently, as shown in FIG. 2F, the carbide material may be carbonized by laser irradiation using a laser oscillator 40 (S15) to form the carbon structure 30' having similar properties to graphene. When high energy laser is irradiated on the carbide material including the photoresist, carbon atoms in the carbide material may bond together or further, form graphene and the other types of materials may be removed by the laser, to form the carbon structure 30'.

When the carbonization process is performed in an atmosphere including oxygen ($O_2$) at least in part, the carbon structure 30' further including graphene oxide, an oxidized form of graphene, may be formed. However, the atmosphere of the carbonization process is not limited to the oxygen ($O_2$) atmosphere, and the laser-assisted carbonization process may be performed in a gas atmosphere including at least one of ordinary air, inert gas, hydrogen or nitrogen.

In some implementations, the laser oscillator 40 may be a carbon dioxide ($CO_2$) laser machine configured to emit a laser of about 10,600 nm wavelength using $CO_2$ gas. However, the type of the laser oscillator 40 is not limited thereto, and the laser oscillator 40 may be other type of machine that may apply energy enough to carbonize carbon in the carbide material into a carbon compound, graphene or graphene oxide by carbon-carbon bond.

The output of the laser oscillator 40 may be properly determined not to completely melt the carbide material layer. In some implementations, the laser oscillator 40 may emit the $CO_2$ laser with the output of about 10 to 12 W, but is not limited thereto.

Additionally, the laser oscillator 40 may repeatedly emit the laser to each region on the carbide material layer while moving the laser irradiation position on the carbide material layer. In some implementations, the laser oscillator 40 may emit the laser to the carbide material layer while moving the laser irradiation position at the speed of about 200 to 500 mm/sec. Additionally, in some implementations, each region of the carbide material layer may be repeatedly exposed to the laser over a few tens of times to a few hundreds of times.

In some implementations, the movement speed of the laser oscillator 40, the amount of laser irradiation by the laser oscillator 40 and/or the output of the laser oscillator 40 may be adjusted to form the carbon structure having planar or 3-dimensional (3D) arrangement. By adjusting the thickness of the carbide material layer and/or the characteristics of the laser, the carbon structure 30' may be formed in planar arrangement like graphene or 3D arrangement including a 3D structure like vertical graphene, thereby achieving selective sensing using adsorption surface having various characteristics.

Figure 2G:
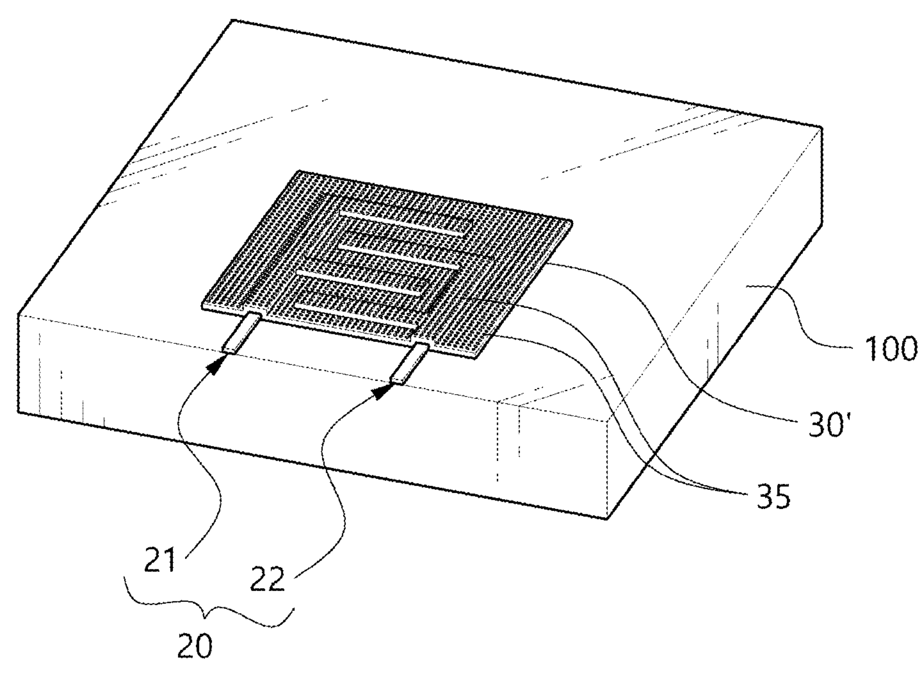

In some implementations, as shown in FIG. 2G, a bonding material layer capable of selectively adsorbing specific gas particles may be formed on the carbon structure 30' to increase selectivity for the corresponding gas particles (S16). The bonding material layer may be in the form of quantum dots 35 of metal oxide, but is not limited thereto. For example, in some implementations, the quantum dots 35 can include molybdenum disulfide ($MoS_2$), zinc oxide ($ZnO_2$), tin oxide ($SnO_2$) and/or tungsten oxide ($WO_3$), and act as a selective functional group to adsorb gas particles on the carbon structure 30', thereby improving the gas adsorption sensitivity of the gas sensor.

The shape and size of the quantum dots 35 shown in the drawings are provided by way of illustration for convenience of description, and do not represent the actual shape or size of the quantum dots 35 as can be easily understood by those skilled in the art.

To form the quantum dots 35 on the carbon structure 30', in some implementations, a dispersion in which the quantum dots 35 of the material for providing selectivity for gas particles, for example, molybdenum disulfide ($MoS_2$), zinc oxide ($ZnO_2$), tin oxide ($SnO_2$) and tungsten oxide ($WO_3$) are dispersed in ethanol may be prepared and applied onto the carbon structure 30'. Subsequently, when the ethanol evaporates, only the quantum dots 35 remain on the carbon structure 30' to obtain the structure as shown in FIG. 2E. In some implementations, after applying the ethanol solution, to evaporate it, the gas sensor may be heated at a predetermined temperature.

However, the method for forming the bonding material for increasing selectivity for gas particles is not limited thereto, and in other implementations, the bonding material layer may be formed on all or a portion of the surface of the carbon structure 30' by Atomic Layer Deposition (ALD), sputtering or other method according to the type of the constituent material.

Although the implementation shown in FIG. 1 shows the quantum dots 35 formed on the carbon structure 30' (S16) after the laser-assisted carbonization (S13) of the photoresist pattern, this is provided by way of illustration, and in other implementation, the bonding material including the quantum dots 35 may be formed on the carbide material layer in other timing.

For example, in the step (S13) of forming the carbide material layer 300, the carbide material layer 300 may be formed by mixing the dispersion in which the bonding material including the quantum dots 35 is dispersed in ethanol with the photoresist solution and applying it onto the substrate 100. When the carbide material layer 300 formed as described above is carbonized by the laser, the ethanol disappears, leaving behind the quantum dots 35 on the carbide material pattern 30', thereby obtaining the equivalent effect as if the quantum dots 35 are formed on the carbon structure 30' at a later time.

The resulting carbon structure 30' includes dangling bonds or imperfect alignment like graphene, and when exposed to specific gas particles, the gas particles are adsorbed onto the lattice defects, i.e., the pores of the carbon structure 30', causing a change in electrical properties (for example, resistance), and therefore, using this feature, it may be possible to achieve the gas sensor capable of detecting hazardous materials. To achieve the gas sensor, a measurement unit (e.g., measurement component, measurement device) may be electrically connected between each comb structure 21, 22 of the electrode pattern 20 to measure the resistance of the electrode pattern 20 (S17).

Figure 3:
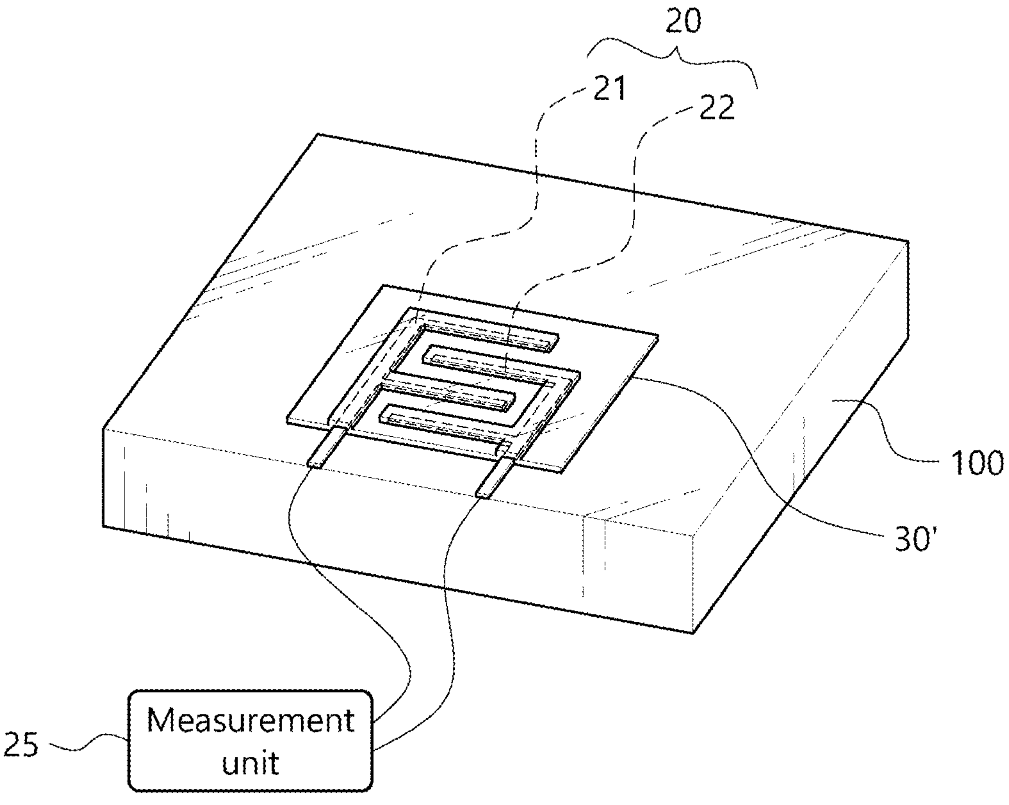
FIG. 3 is a diagram of an example of a gas sensor.

FIG. 3 is a diagram of an example of the gas sensor.

Referring to FIG. 3, the gas sensor may include the electrode pattern 20, the carbon structure 30' located on the electrode pattern 20 and including the pores for adsorption of gas particles, and the measurement unit 25 electrically connected to the electrode pattern 20 to measure the electrical properties (for example, resistance) of the electrode pattern 20. The unit as used herein is intended to include a hardware means for accomplishing a specific function and/or a software means stored and executed by the hardware means.

In some implementations, the electrode pattern 20 has an electrode shape formed by the pair of comb structures 21, 22 engaged with each other. Since the carbon structure 30' is located on the electrode pattern 20 and electrically connected to the electrode pattern 20, when gas particles are adsorbed on the carbon structure 30', there is a change in electrical properties of the electrode pattern 20 such as resistance between each comb structure 21, 22 of the electrode pattern 20.

Although not shown in the drawings, the gas sensor according to an implementation may further include the bonding material located on the carbon structure 30' and capable of providing selectivity for gas particles, for example, molybdenum disulfide ($MoS_2$), zinc oxide ($ZnO_2$), tin oxide ($SnO_2$) and tungsten oxide ($WO_3$) or a layer of the bonding material. For example, the bonding material may be located on the carbon structure 30' in the form of at least one quantum dot.

When the gas sensor is exposed to gas particles such as hazardous materials, the gas particles are adsorbed onto the carbon structure 30', causing a change in electrical resistance between the comb structures 21, 22 of the electrode 20. The measurement unit 25 may be electrically connected to the electrode pattern 20 through an electrical wire to measure the resistance change of the electrode pattern 20, thereby detecting the gas particles near the gas sensor.

That is, when the gas particles are bound to the carbon structure 30', the resistance between the comb structures 21, 22 of the electrode 20 changes, and the measurement unit 25 may detect the presence of gases and/or the concentration of gases. In some implementations, the resistance change of the electrode pattern 20 caused by the adsorption of the gas particles on the carbon structure 30' may vary depending on the type of gases to be measured, and the measurement unit 25 may pre-store data associated with the presence or absence of gases and/or the gas concentration value based on the resistance change for each type of gas and measure the presence or absence and/or concentration of gases near the carbon structure 30' using the data.

For example, in case nitrogen oxide ($NO_x$) such as nitrogen dioxide ($NO_2$) is present near the gas sensor, when gas particles are adsorbed onto the carbon structure 30', the measurement unit 25 may pre-store data associated with the resistance value of the electrode pattern 20 or changes in resistance value for each concentration of nitrogen oxide ($NO_x$), and generate an output value of the presence or absence and/or concentration of nitrogen oxide ($NO_x$) by comparing the currently measured resistance value of the electrode pattern 20 or its change with the pre-stored data for each concentration.

Figure 4:
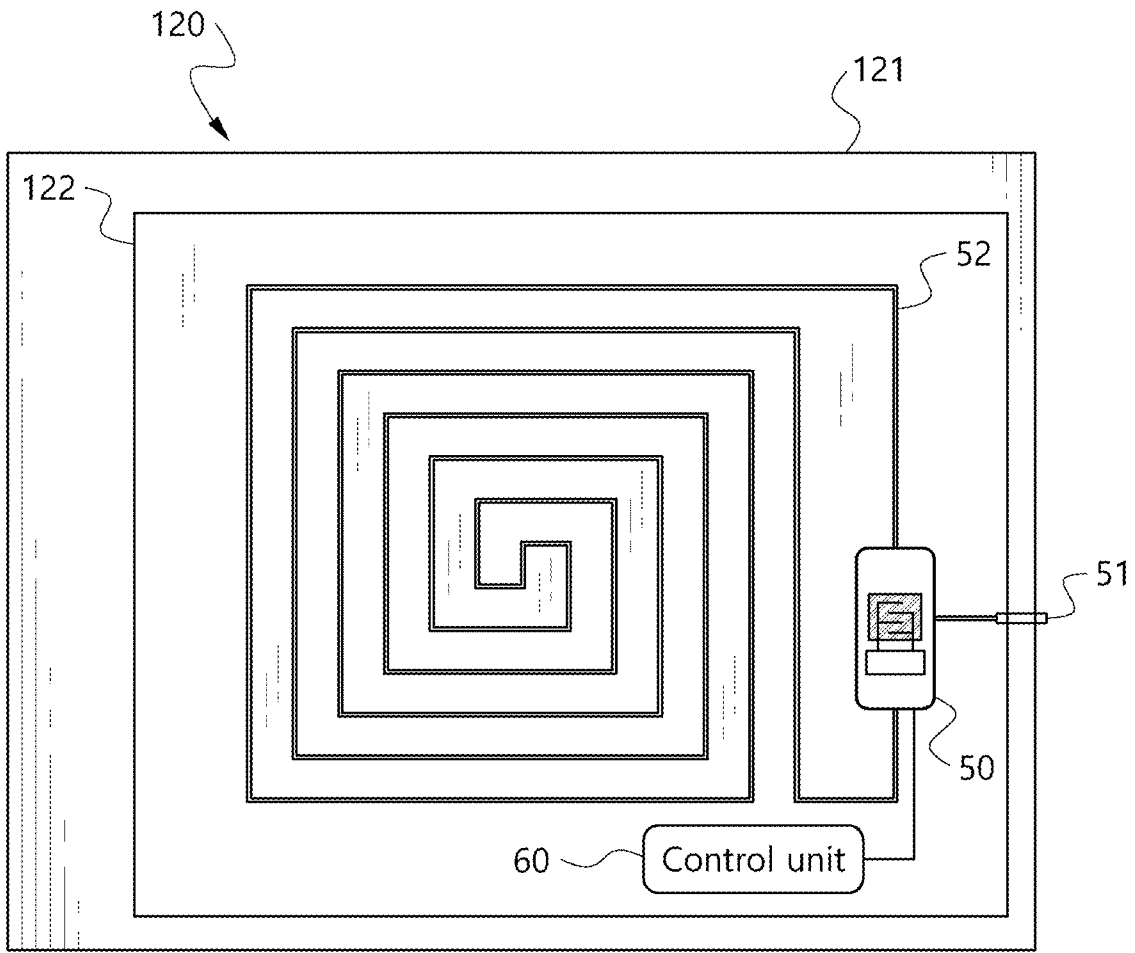
FIG. 4 is a diagram of an example of a detection device including a gas sensor.

FIG. 4 is a diagram of an example of a detection device including the gas sensor.

Referring to FIG. 4, the gas sensor 50 may be integrated with one or more other modules into the detection device 120. For example, the detection device 120 may have a structure in which the gas sensor 50, a control unit 60 to control the supply of gaseous phase materials to the gas sensor 50, and a material transport pipe 52 corresponding to a separation module for separation of gas particles to be detected can be integrated on a substrate 122 and installed within a body 121. In some implementations, the detection device 120 may have a portable small size.

The substrate 122 may be made of silicon, glass or other appropriate material, and at least one of a conduit 51 or the material transport pipe 52 connected to the gas sensor 50 may be formed by etching a surface of the substrate by a Deep Reactive-Ion Etching (DRIE) process. In this case, it may be possible to finely form a structure having a nanometer level of size on the substrate 122, thereby minimizing the total size of the detection device 120.

The conduit 51 is the component through which gaseous phase materials including gases to be measured are fed into the gas sensor 50 from the ambient air around the detection device 120 or a gas tank. On the other hand, the material transport pipe 52 is configured to separate the gases to be measured into each component. The gas particles fed through the conduit 51 undergo concentration upon adsorption on the carbon structure of the gas sensor 50. In the gas sensor 50 according to implementations, since the carbon structure has high specific surface area through carbon bonds arranged in a planar or 3D configuration, there is an advantage of high preconcentration factor for gas particles.

Subsequently, when the gas feed through the conduit 51 is interrupted and the carbon structure is heated at the predetermined temperature, the gas particles are desorbed from the carbon structure, and in this instance, when a flow of gaseous phase materials is formed using carrier gas, the constant speed carrier gas may carry the desorbed gas particles, and the gas particles may be separated into each component at a time interval while moving in the material transport pipe 52 having a very long path.

That is, the material transport pipe 52 is in fluid communication with the gas sensor 50 and defines a separation path along which the gases passing through the gas sensor 50 move upon entering. The gas particles may be separated according to the type of material in a way that they move in the separation path of the material transport pipe 52 at different movement speeds depending on the type of material and exit the material transport pipe 52 at a time interval.

According to an implementation, for the gas movement path in the material transport pipe 52 to have a sufficiently long path to separate hazardous materials, the material transport pipe 52 may be disposed to form a single layer of columns bent in a maze shape within a preset square or rectangular space. As shown in FIG. 4, the material transport pipe 52 may bend and extend to the center of the square or rectangular space in the shape of a sort of coil and extend back from the center in the contrary direction in the coil shape.

When the flow of carrier gas is formed in a direction within the material transport pipe 52, the gas particles may pass through the path extending in a serpentine pattern toward the center in the column shape and the path extending away from the center in a sequential order, and while moving along the maximized path in the limited space, they may be separated into types of gases.

That is, the gas sensor according to implementations of the present disclosure may act as an adsorbent for adsorption and preconcentration of gas particles with high efficiency. Additionally, the adsorption may be adequately performed at room temperature. Since the gas sensor according to implementations exhibits the unique resistance change (increase or decrease) of the sensor determined by the structure and shape of the carbon structure when gas particles are bound, it may be possible to easily detect the presence or absence and concentration of specific gases such as hazardous materials through the measurement of the resistance value or the resistance change value of the gas sensor.

Further, the gas sensor according to implementations may work to desorb the adsorbed gas particles from the carbon structure when heated at the predetermined temperature. Using this feature, at room temperature, the gas sensor may be used as an adsorbent for adsorption of the gaseous phase materials, and when detailed analysis of the adsorbed gas particles is necessary, the detailed analysis of the type and/or concentration of the gas particles may be performed by desorbing the gas particles and transporting them through the separation path in the material transport pipe 52.

In this instance, the material transport pipe 52 may be connected to the gas sensor 50 to allow the gas particles passing through the separation path to flow into the gas sensor 50 again. For example, when the gaseous phase materials start moving from the gas sensor 50 of FIG. 4 toward the top of the drawing, the gas particles in the gaseous phase materials may be separated into types of gases while moving to the center of the square or rectangular space along the material transport pipe 52 and then moving in the outward direction of the square or rectangular space from the center, and each type of gas particle may enter the gas sensor 50 again from the bottom of the drawing at a time interval.

In this case, the gas sensor 50 may perform preconcentration of specific gas particles such as hazardous materials in the gaseous phase materials, and at the same time, when the gaseous phase materials passing through the gas sensor 50 are separated through the microcolumn-type material transport pipe 52 and enters the gas sensor 50 again, may detect the presence and/or concentration of the specific gas particles such as hazardous materials from the gaseous phase materials. The detection device including the gas sensor 50 and the material transport pipe 52 may have a simpler configuration than the conventional detection device made up of three elements of [preconcentration], [separation] and [sensing].

The control unit 60 may include a processor to control the gas feed through the conduit 51 and the operation of the gas sensor 50 to achieve preconcentration of the gas particles and detection of each of the gas particles separated into types using the gas sensor 50. Additionally, the control unit 60 may further include a memory to store information such as data associated with the resistance value of the gas sensor 50 or the change in resistance value according to the concentration of gases for each type of gases, and the processor of the control unit 60 may determine the type and concentration of gases detected by the gas sensor 50 based on the information stored in the memory.

However, this is provided by way of illustration, and in other implementation, the above-described function of the control unit 60 may be performed by a computer that is not integrated with the gas sensor 50, and in this case, the detection device 120 may transmit the detection result of the gas sensor 50 to the computer via communication with the computer to enable the computer to process the same.

Further, a power source to supply the power to the gas sensor 50 and the control unit 60, a communication module to transmit the detection result of the gas sensor 50 in the form of a signal, and an output device, for example, a speaker or a liquid crystal display to notify an operator of the detection result of the gas sensor 50 may be further mounted on the body 121.

Figure 5:
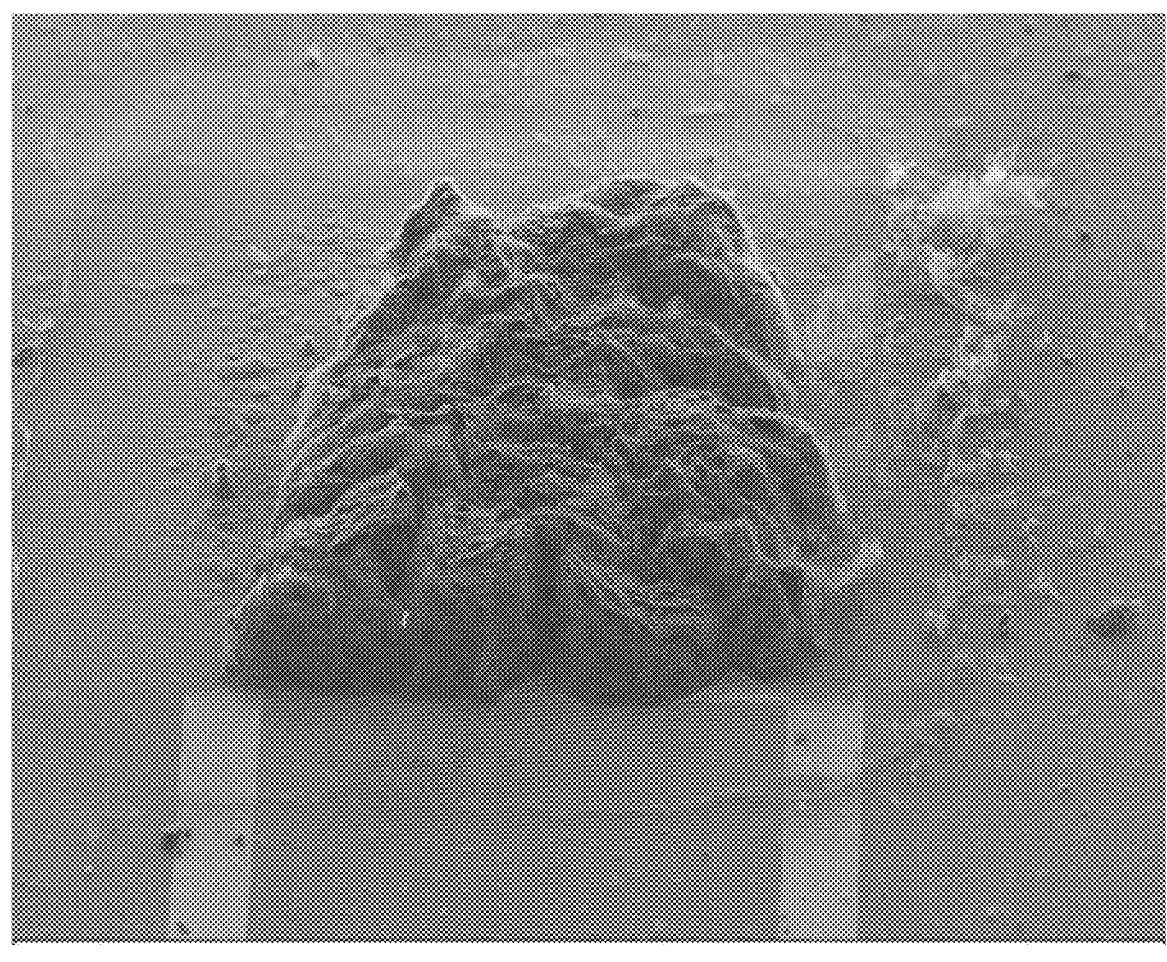
FIG. 5 is an example of a Scanning Electron Microscopy (SEM) image of a carbon structure.

FIG. 5 is an example of a Scanning Electron Microscopy (SEM) image of a carbon structure.

In the gas sensor (e.g., the gas sensor 50) according to implementations, as described above, the carbon structure is generated by carbonizing the photoresist such as SU-8 or other carbide material using an energy emission means such as the $CO_2$ laser.

The SEM image of the accompanying FIG. 5 exemplarily illustrates the shape change of the carbon structure by the adjustment of the preset speed, the amount of laser irradiation and the output of the laser oscillator, but is not intended to depict different implementations.

Referring to FIG. 5, the resulting carbon structure may include a carbon compound, graphene and/or graphene oxide by carbon-carbon bond. Additionally, the carbon structure may have a structure in which these materials are arranged in the plane direction, and a 3D arrangement in which the arrangement of the materials is extended in the vertical direction. The carbon structure is characterized by including the pores and arrangement defects such as dangling bonds, leading to adsorption of gas particles on the surface of the carbon structure or the pores in the carbon structure.

By measuring the electrical properties of the carbon structure by the measurement unit of the gas sensor, it may be possible to detect the presence or absence and/or concentration of the gas particles adsorbed on the carbon structure.

Figure 6A:
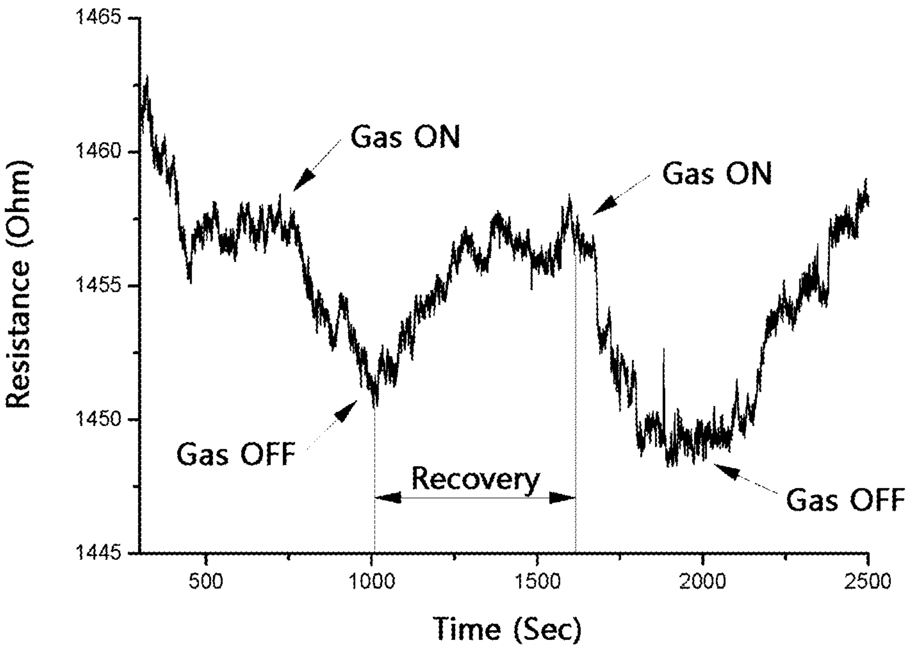
FIGS. 6A and 6B are graphs illustrating an example of resistance change over time when a gas sensor including the carbon structure illustrated in FIG. 5 is exposed to target gases.
Figure 6B:
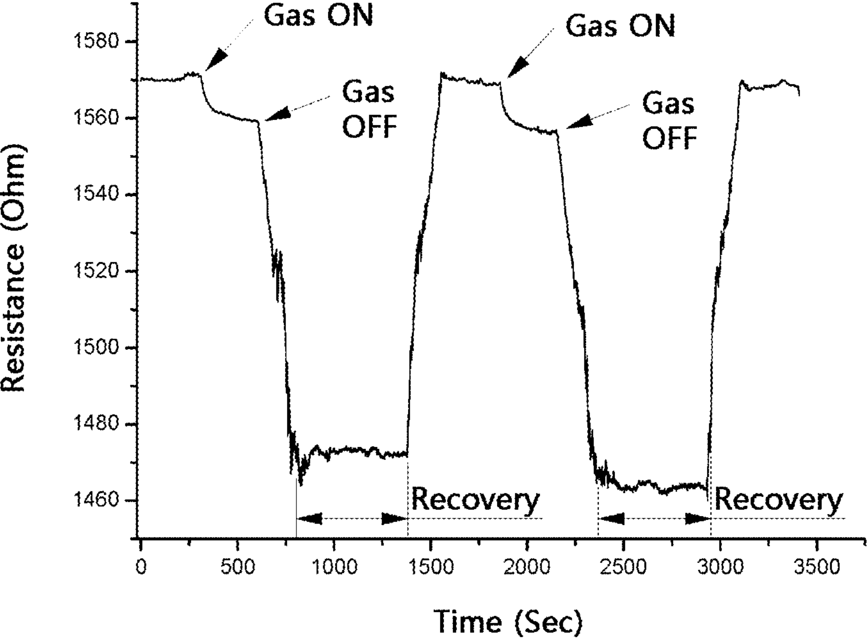

FIGS. 6A and 6B are graphs illustrating an example of resistance change over time when the gas sensor including the carbon structure illustrated in FIG. 5 is exposed to target gases.

In the gas sensor including the carbon structure and having the resistance of about 1.49 kΩ at room temperature, FIG. 6A shows resistance change when the carbon structure is exposed to 4 ppm of nitrogen oxide ($NO_x$) gas, and the arrow on the graph indicates the start time of gas supply to the carbon structure (i.e., Gas ON time) and the time when the gas supply to the carbon structure is stopped (i.e., Gas OFF time). In this instance, the carbon structure may be heated at the predetermined temperature, and FIG. 6A shows resistance change of the gas sensor when the carbon structure is heated at 200° C.

In some implementations, for the supply of gaseous phase materials to the gas sensor, the gas supply to the carbon structure may be adjusted to have (1) an idling range in which heating is only performed without gas supply for a predetermined time (for example, 10 minutes), (2) a feed range in which gases are supplied for a predetermined time (for example, 5 minutes) and (3) a recovery range in which gas particles are desorbed from the carbon structure for a predetermined time (for example, 10 minutes) after the gas feed is stopped. In this instance, the feed range and the recovery range may be repeatedly performed multiple times.

As a result, as shown in FIG. 6A, in the feed range, the gas particles are adsorbed onto the carbon structure and the resistance of the gas sensor reduces, and in the recovery range, when the predetermined time passes after the gas supply is stopped, the gas particles are desorbed from the carbon structure and the resistance of the gas sensor returns to a value close to the resistance before the gas adsorption.

Additionally, FIG. 6B shows resistance change of the gas sensor when the same carbon structure is exposed to 4 ppm of nitrogen oxide ($NO_x$) gas wherein the gas supply is adjusted to have (1) 5-minute idling range, (2) 5-minute feed range and (3) 10-minute recovery range. In some implementations, in the recovery range in which the feed of nitrogen oxide ($NO_x$) is stopped, inert gas, for example, nitrogen ($N_2$) gas may be fed into the gas sensor, but is not limited thereto.

In the experiment shown in FIG. 6B, the idling range and the feed range are performed at room temperature (for example, 25° C.), and after the temperature increases from room temperature to 200° C., the temperature is maintained at 200° C. in the recovery range. After the gas feed is stopped, the resistance of the gas sensor reduces due to the temperature change, and in the recovery range in which the temperature is maintained at 200° C., the resistance is constantly maintained at relatively lowest value. However, the resistance change in the recovery range after the gas feed is stopped and the heating temperature for forming the recovery range may be different according to implementations, and is not limited to the above-described example.

Figure 7:
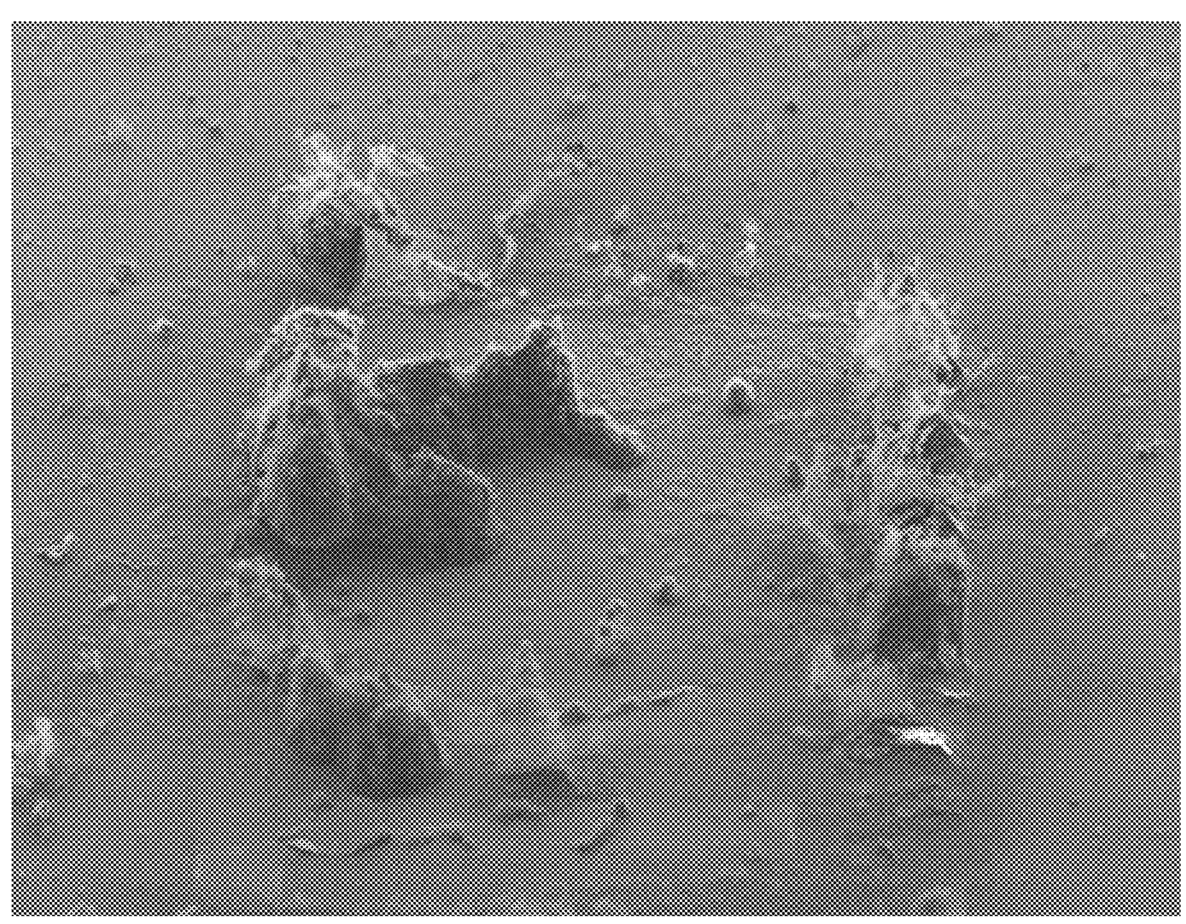
FIG. 7 is an example of an SEM image of a carbon structure.

FIG. 7 is an example of an SEM image of the carbon structure formed in a different shape from FIG. 5. In the method for manufacturing the gas sensor according to implementations, the shape of the carbon structure may be changed by adjusting the type, amount, intensity and/or duration of laser (for example, oscillator movement speed) in the carbonization of the carbide material, and accordingly the electrical properties may change. The gas sensor including the carbon structure shown in FIG. 7 has the resistance of about 1.88 kΩ at room temperature.

FIGS. 8A to 8D are graphs illustrating an example of resistance change over time when the gas sensor including the carbon structure shown in FIG. 7 is exposed to target gases.

Figure 8A:
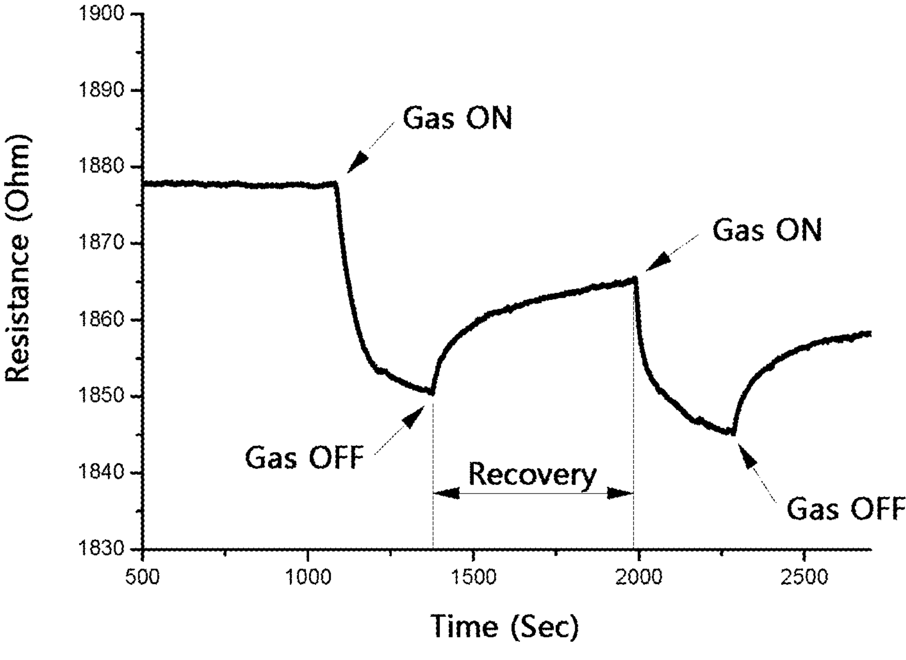
FIGS. 8A to 8D are graphs illustrating an example of resistance change over time when a gas sensor including the carbon structure shown in FIG. 7 is exposed to target gases.
Figure 8B:
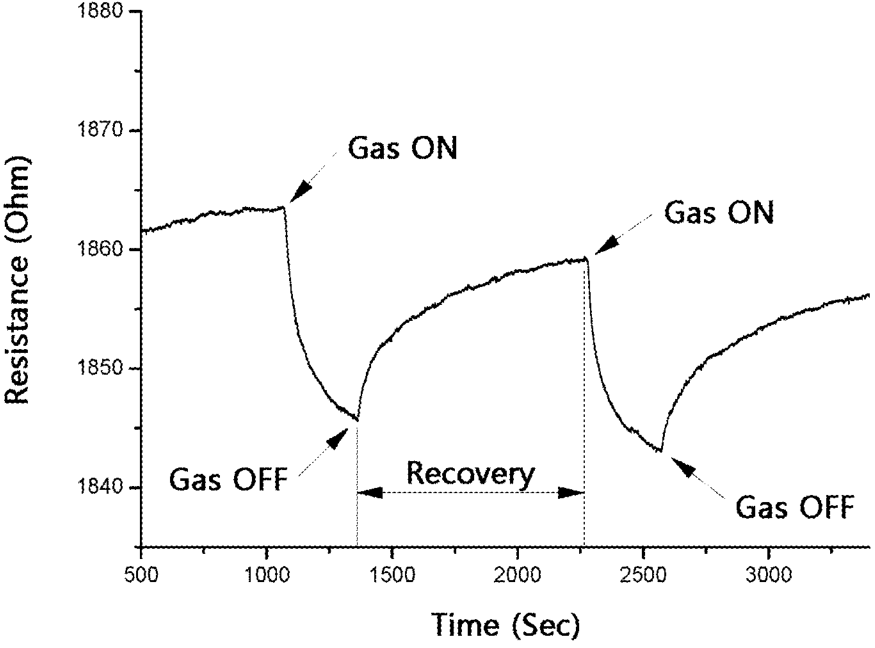

FIG. 8A shows resistance change of the gas sensor when the carbon structure is exposed to 4 ppm of nitrogen oxide ($NO_x$) gas wherein the gas supply is adjusted to have (1) 15-minute idling range, (2) 5-minute feed range and (3) 10-minute recovery range. Additionally, FIG. 8B shows resistance change of the gas sensor when the same carbon structure is exposed to 2 ppm of nitrogen oxide ($NO_x$) gas and the gas supply is adjusted to have (1) 15-minute idling range, (2) 5-minute feed range and (3) 15-minute recovery range. In this instance, the temperature of the carbon structure is maintained at 200° C.

Figure 8C:
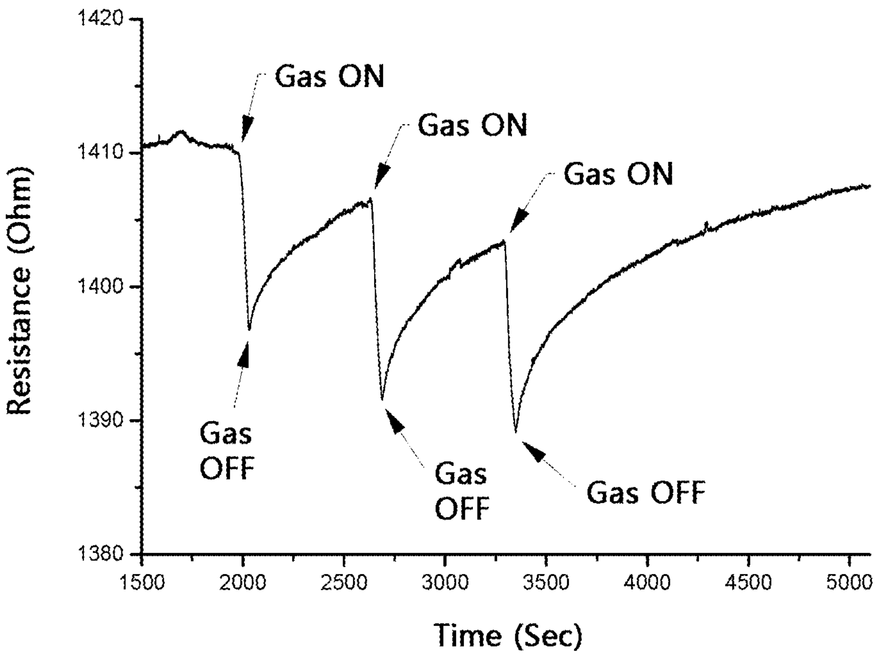
Figure 8D:
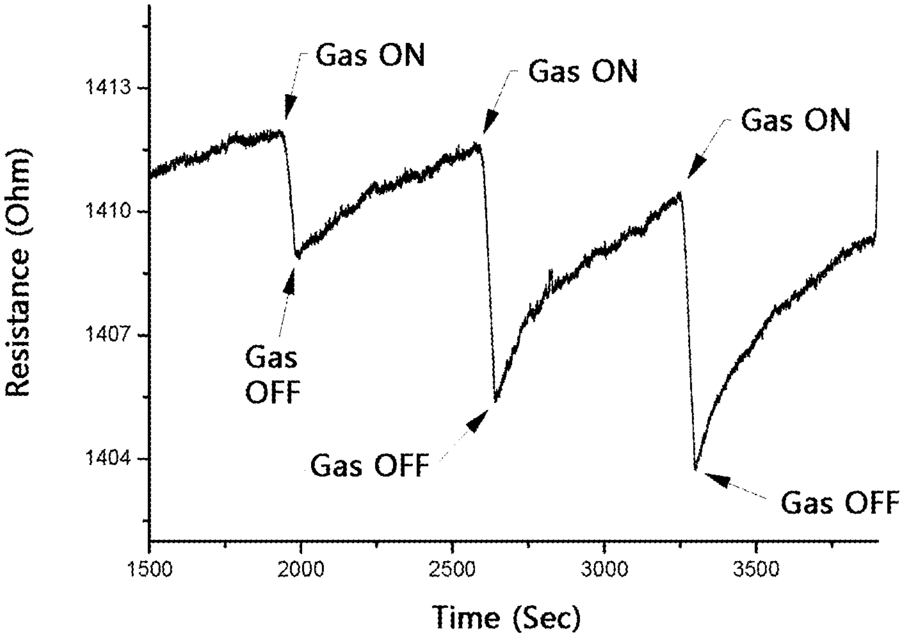

Additionally, FIG. 8C shows resistance change of the gas sensor when the same carbon structure is exposed to nitrogen oxide ($NO_x$) gas wherein in a state that the concentration of nitrogen oxide ($NO_x$) in gases is reduced to 1 ppm and the temperature is maintained at 200° C., gases are supplied for 1 minute each time in the feed range and when the gas supply is stopped, 10-minute recovery range is given each time. Further, FIG. 8D shows resistance change of the gas sensor when the concentration of nitrogen oxide ($NO_x$) is further reduced to 0.5 ppm in the same conditions as the experimental results shown in FIG. 8C.

Figure 9:
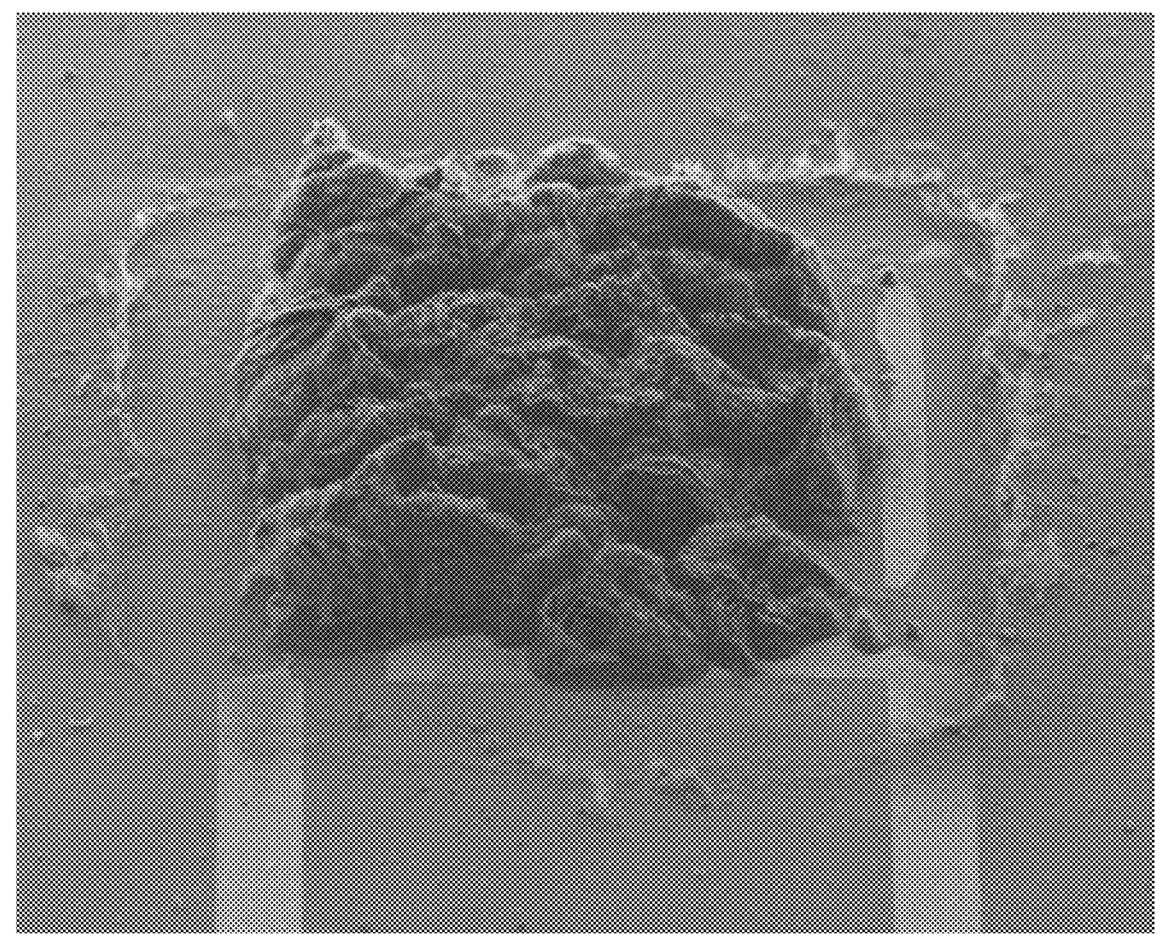
FIG. 9 is an example of an SEM image of a carbon structure.

FIG. 9 is an example of an SEM image of the carbon structure formed in a different shape from FIG. 5.

Figure 10:
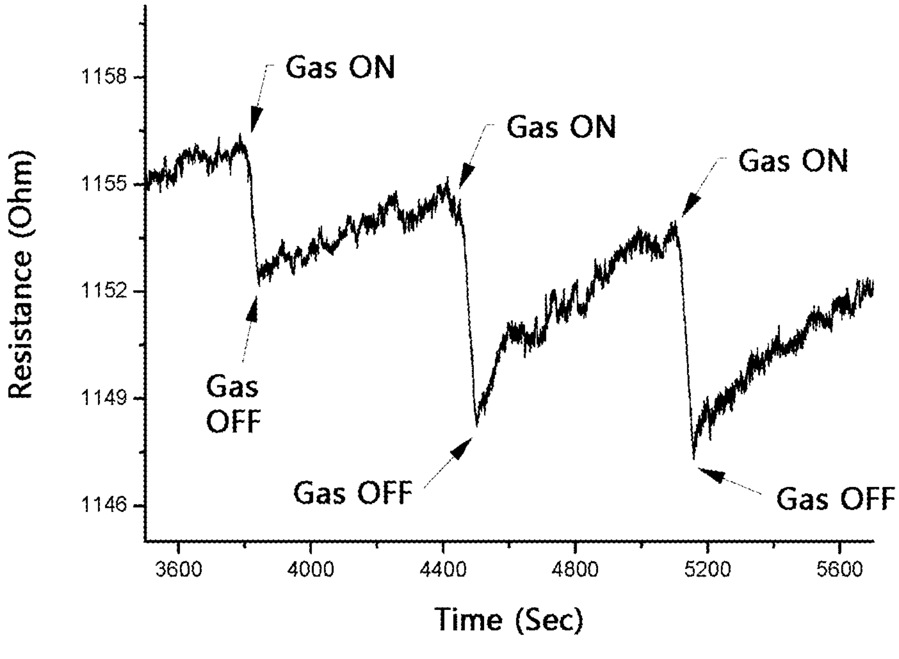
FIG. 10 is a graph showing an example of resistance change over time when a gas sensor including the carbon structure shown in FIG. 9 is exposed to target gases.

FIG. 10 is a graph showing an example of resistance change over time when the gas sensor including the carbon structure shown in FIG. 9 is exposed to target gases.

FIG. 10 shows resistance change of the gas sensor when the carbon structure shown in FIG. 9 is exposed to 1 ppm of nitrogen oxide ($NO_x$) gas wherein in a state that the temperature is maintained at 200° C., gases are supplied for 1 minute each time in the feed range and when the gas supply is stopped, 10-minute recovery range is given each time.

Figure 11:
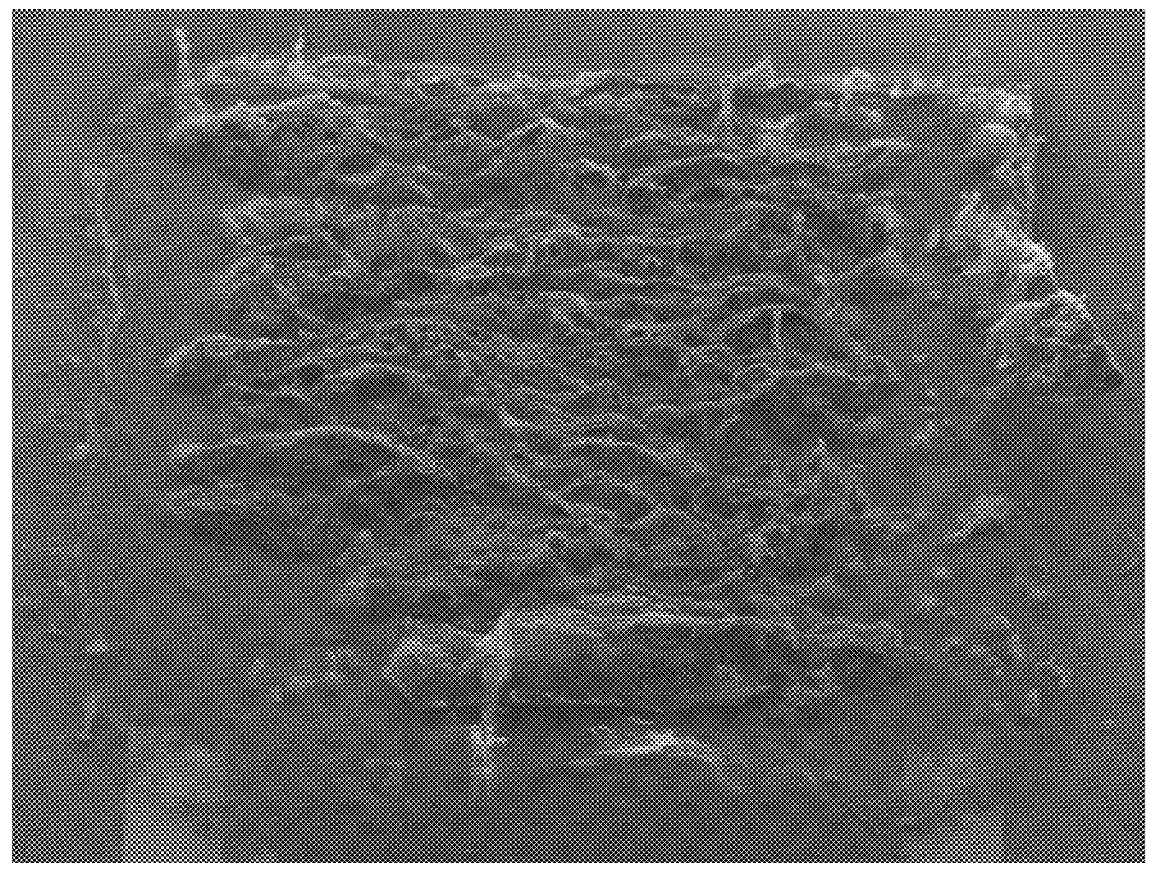
FIG. 11 is an example of an SEM image of a carbon structure.
Figure 12A:
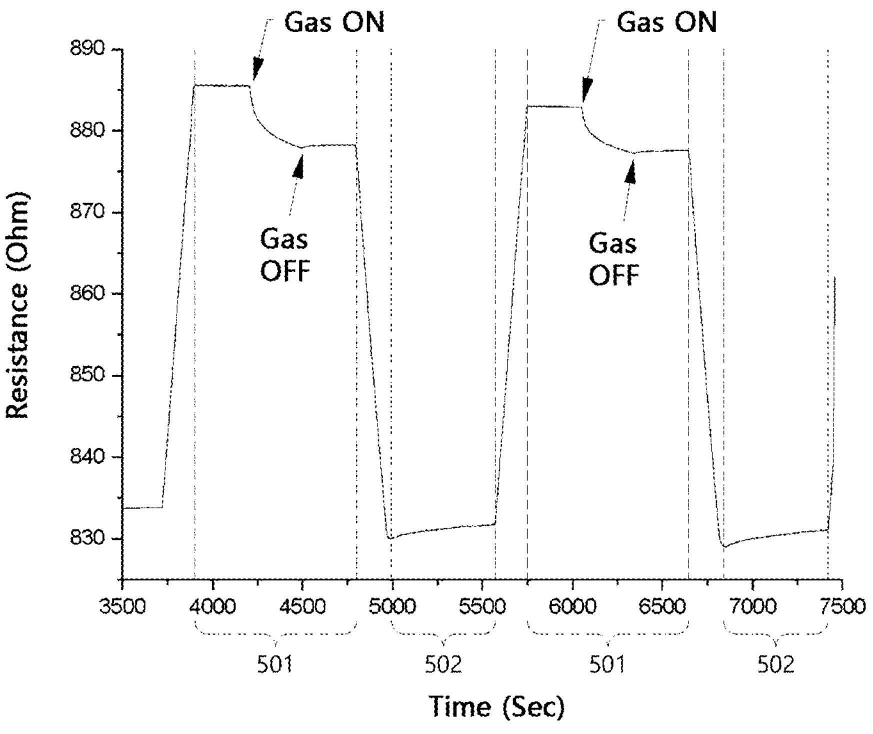
FIGS. 12A and 12B are graphs illustrating examples of resistance change over time when a gas sensor including the carbon structure shown in FIG. 11 is exposed to target gases.
Figure 12B:
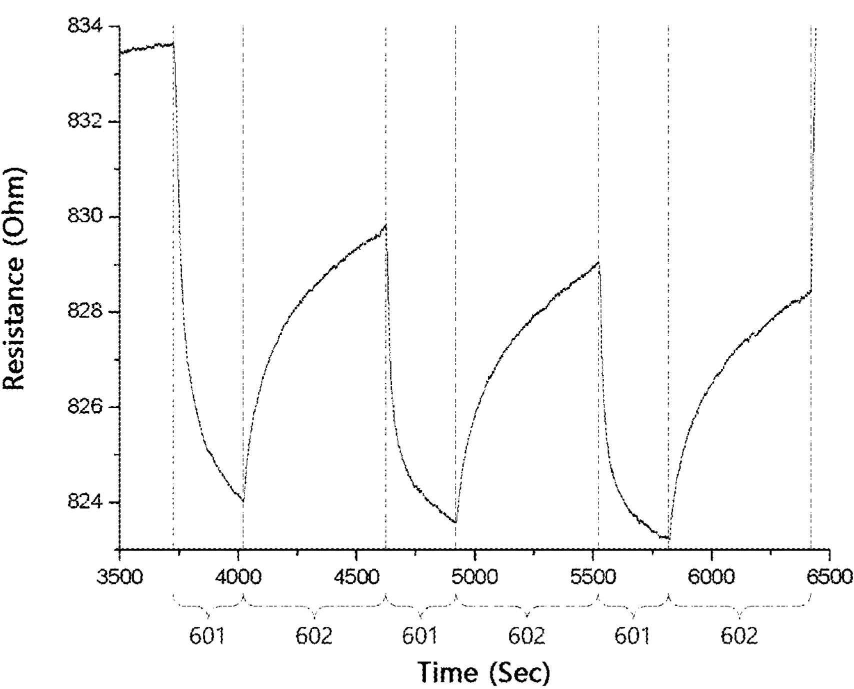

FIG. 11 is an example of an SEM image of the carbon structure formed in a different shape from FIG. 5. FIGS. 12A and 12B are graphs illustrating examples of resistance change over time when the gas sensor including the carbon structure shown in FIG. 11 is exposed to target gases.

FIG. 12A shows resistance change of the gas sensor when the carbon structure shown in FIG. 11 is exposed to 1 ppm of nitrogen dioxide ($NO_2$) gas wherein the temperature is maintained at room temperature (for example, 25° C.) in the time range 501 including the gas feed range, and the recovery range 502 is given in which after the gas feed is stopped, the temperature increases to 200° C. and the corresponding temperature is maintained for a predetermined time. As shown, gas particles adsorbed on the carbon structure at room temperature are desorbed as the temperature increases, and the resistance of low value is uniformly maintained in the recovery range 502. FIG. 12B shows resistance change of the gas sensor when the carbon structure shown in FIG. 11 is exposed to 1 ppm of nitrogen dioxide ($NO_2$) gas at the temperature of 200° C. wherein the gas feed range 601 for about 5-minutes and the recovery range 602 for about 10 minutes after the gas feed is stopped are given in an alternating manner. As shown, the resistance change of the gas sensor in each range is clearly seen.

Figure 13:
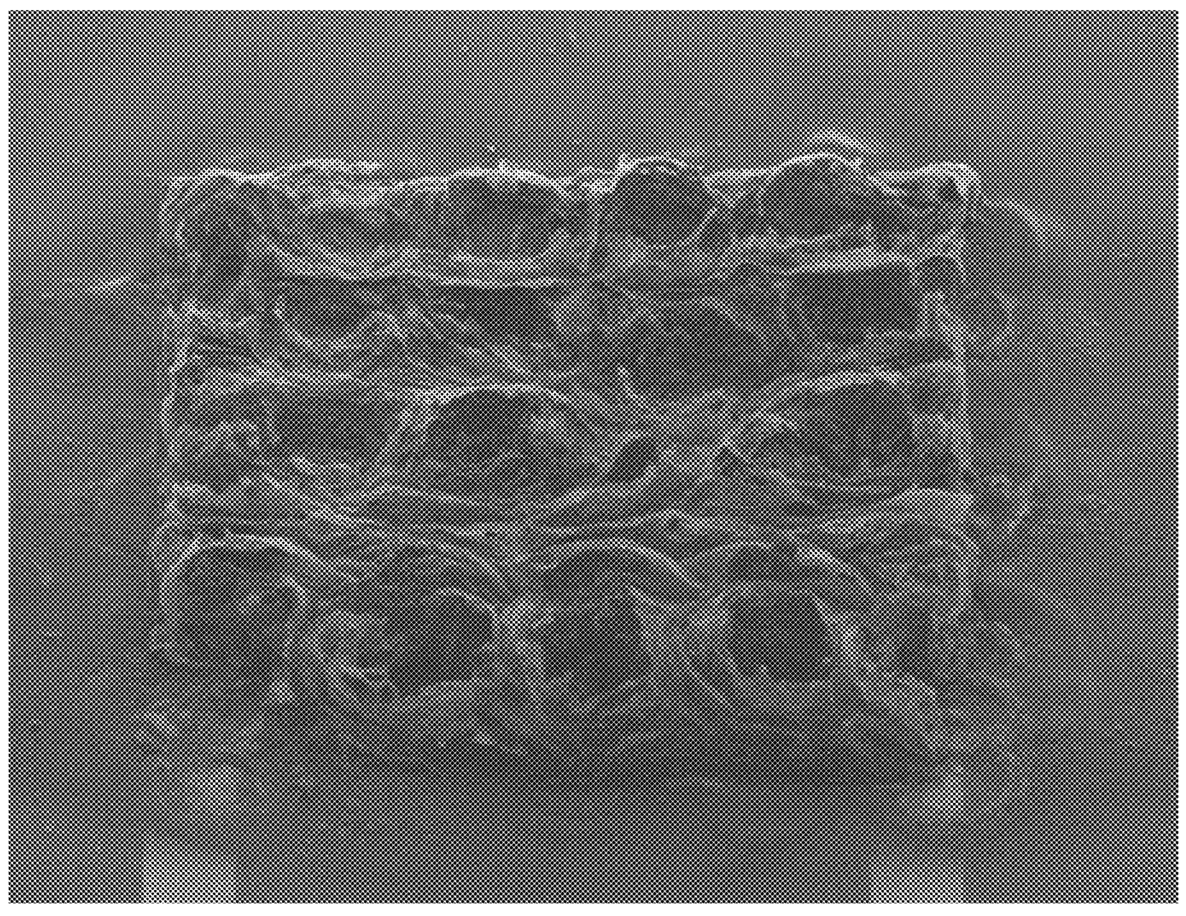
FIG. 13 is an example of an SEM image of a carbon structure.
Figure 14A:
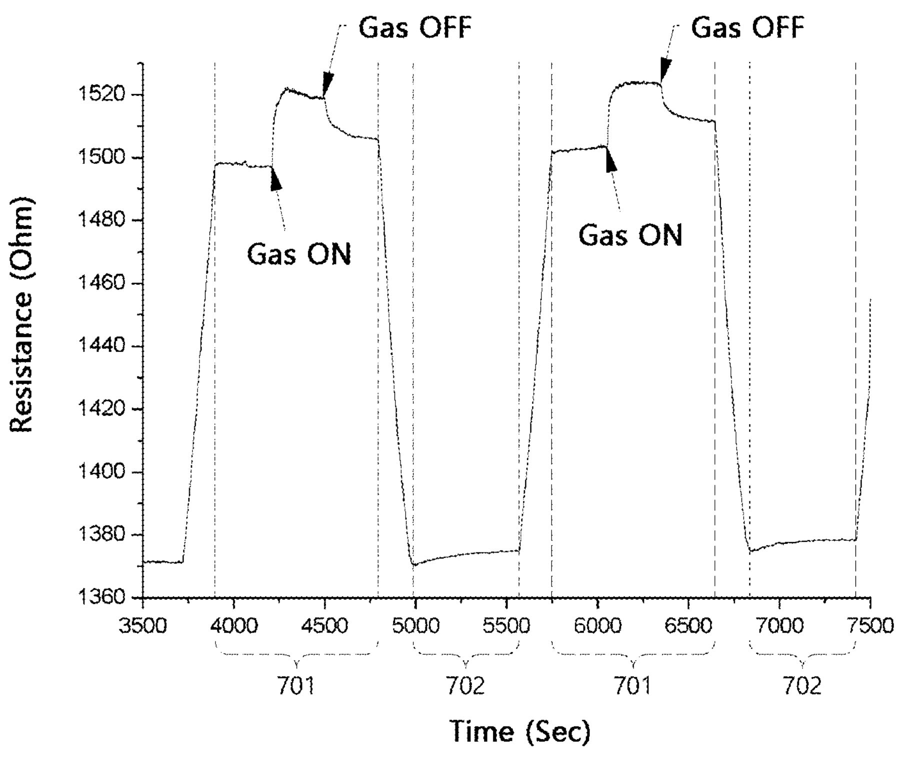
FIGS. 14A and 14B are graphs illustrating examples of resistance change over time when a gas sensor including the carbon structure shown in FIG. 13 is exposed to target gases.
Figure 14B:
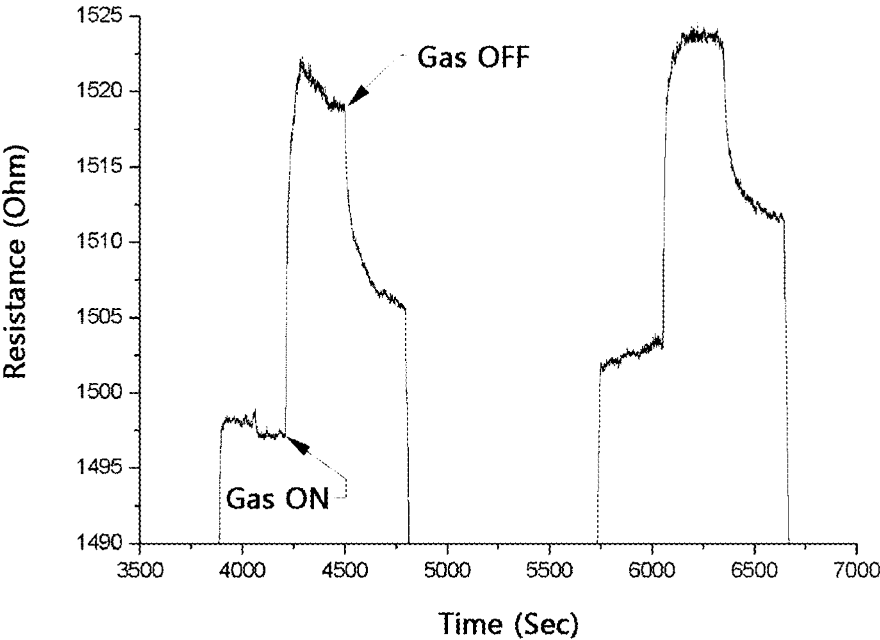

FIG. 13 is an example of an SEM image of the carbon structure formed in a different shape from FIG. 5. FIGS. 14A and 14B are graphs illustrating examples of resistance change over time when the gas sensor including the carbon structure shown in FIG. 13 is exposed to target gases.

The carbon structure shown in FIG. 13 is made by laser irradiation on a specific point for a relatively long time in the laser irradiation process for carbonization, so that one or more focal points of the laser are arranged. FIG. 14A shows resistance change of the gas sensor when the carbon structure is exposed to 2 ppm of nitrogen dioxide ($NO_2$) gas wherein the temperature is maintained at room temperature (for example, 25° C.) in the time range 701 including the gas feed range and after the gas feed is stopped, the temperature increases to 200° C., and then the recovery range 702 for about 10 minutes is given at the corresponding temperature.

Additionally, FIG. 14B shows resistance change of the gas sensor when the carbon structure shown in FIG. 13 is exposed to 2 ppm of nitrogen dioxide ($NO_2$) gas while the temperature is maintained at 200° C. As shown, as opposed to the above-described implementations, the gas sensor has an increase in resistance by the adsorption of gas particles. The resistance change of the gas sensor according to implementations may vary depending on the actual sensor structure formation, and the adsorbed amount of gas particles on the gas sensor may be detected by quantifying and prestoring each of the unique resistance change characteristics of the sensor.

Figure 15A:
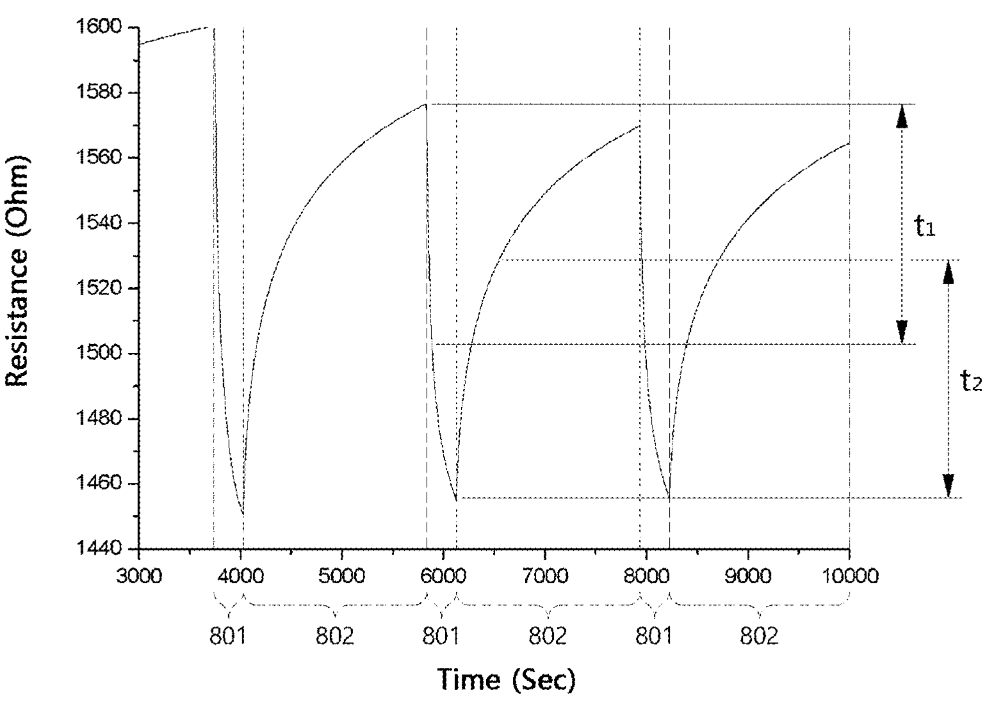
FIGS. 15A and 15B are graphs illustrating examples of resistance change as a function of heating temperature of a gas sensor.
Figure 15B:
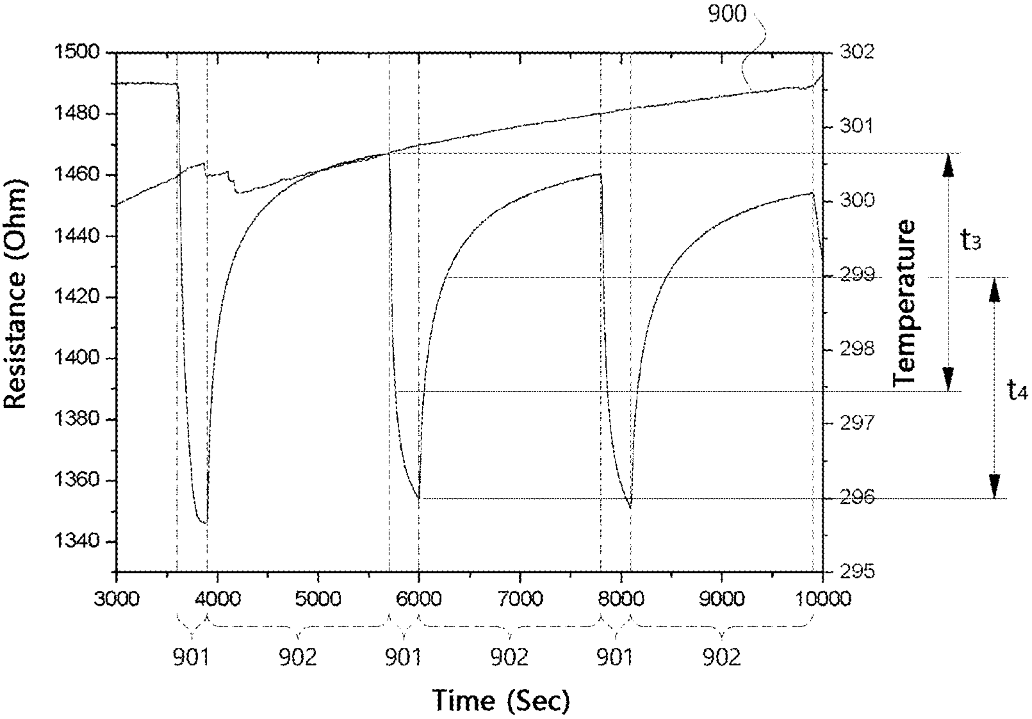

FIGS. 15A and 15B are graphs illustrating examples of resistance change as a function of heating temperature of the gas sensor.

FIG. 15A shows resistance change of the gas sensor in 5-minute feed range 801 in which 1 ppm of nitrogen dioxide ($NO_2$) gas is supplied at the temperature of 200° C. and 30-minute recovery range 802 in which the gas supply is stopped, and FIG. 15B shows resistance change of the gas sensor in the feed range 901 and the recovery range 902 when the temperature 900 increases to 300° C. in the same conditions.

In FIG. 15A, the length of the reaction time ($t_1$) during which the resistance reduces by the adsorption of gas particles is about 66.7 seconds and the length of the recovery time ($t_2$) during which the resistance is recovered by the desorption of gas particles is about 408 seconds. In this instance, the reaction time and the recovery time refer to the time required for the unique response to reduce to 1/e by the adsorption of gas particles (or referred to as the time constant). That is, the reaction time refers to the time required for the resistance to reduce 1/e folds of the initial resistance value by the adsorption of gas particles, and the recovery time refers to the time required for the resistance to increase (1-1/e) folds of the final resistance value by the desorption of gas particles.

In contrast, in FIG. 15B, when the temperature increases to 300° C., the length of the reaction time ($t_3$) is about 50 seconds and the length of the recovery time ($t_4$) is about 210 seconds, and it is confirmed that as the temperature is higher, the reaction time and recovery time of the gas sensor are shorter. However, the operating temperature of the gas sensor may be differently set according to implementations, and is not limited to the specific temperature.

Figure 16:
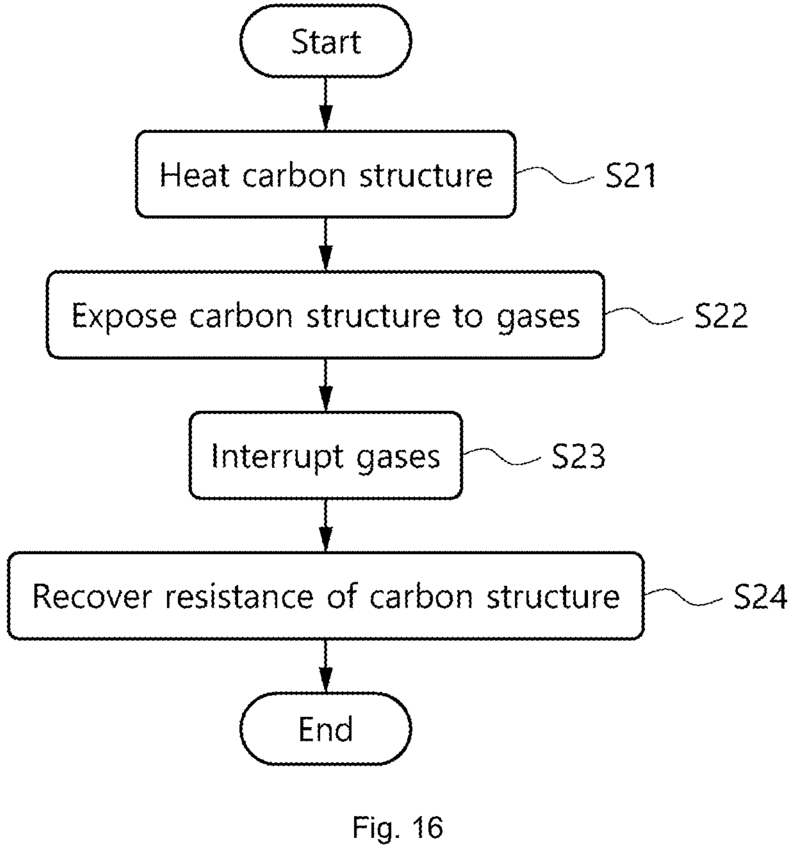
FIG. 16 is a flowchart illustrating example method of operating a gas sensor.

FIG. 16 is a flowchart illustrating example method of operating a gas sensor, and the operation process of the gas sensor described above with respect to FIGS. 5 to 15B can correspond to one or more implementations of the operation method of the gas sensor shown in FIG. 16.

Referring to FIG. 16, the carbon structure of the gas sensor may be heated at the preset temperature (S21). This is to adsorb gas particles onto the carbon structure, and for example, the carbon structure may be heated in the idling range for about 5 minutes to 15 minutes before the gas feed into the carbon structure. In this instance, the heating temperature may be any temperature determined within the temperature range between room temperature and a few hundreds of ° C.

Subsequently, the carbon structure heated at the predetermined temperature may be exposed to gaseous phase materials including gases to be detected (S22). This corresponds to the feed range described above with reference to FIGS. 5 to 10, and the length of time of the feed range may be properly determined according to the extent of adsorption reaction between the gas particles to be detected and the carbon structure. In some implementations, the carbon structure may be exposed to the gaseous phase materials for 1 minute to 5 minutes. The specific gas particles may be detected by the gas sensor by measuring the resistance change of the gas sensor in the feed range.

For example, when the specific gas particles, for example, nitrogen oxide ($NO_x$) or other types of hazardous materials are adsorbed onto the carbon structure, the measurement unit of the gas sensor may pre-store data associated with the resistance value of the gas sensor or changes in resistance value of the gas sensor by the concentration of gas particles, and detect the presence or absence and/or concentration of the specific gas particles by comparing with the resistance change in the feed range.

In some implementations, for repeated measurements, the gas feed into the carbon structure may be interrupted (S23), and in this case, the gas sensor may be recovered to the resistance that is equal or close to the previous level by the desorption of the adsorbed gas particles from the carbon structure after the elapse of time (S24). This corresponds to the recovery range described above with reference to FIGS. 5 to 10. In some implementations, the recovery range may last for 5 minutes to 15 minutes.

In this instance, the length of the feed range, the heating temperature of the carbon structure and/or the length of the recovery range may be properly determined such that the resistance of the gas sensor is sufficiently recovered in the recovery range. For example, in general, as the length of the recovery range is longer, the extent of resistance recovery improves, and thus the length of time of the recovery range may be determined such that there is no or little resistance change of the gas sensor in the initial feed range and the feed range after recovery.

Additionally, the gas supply to the carbon structure may be adjusted to repeatedly perform the feed range and the recovery range one or more times. In this instance, since noise in resistance measurement tends to increase due to particles remaining on the carbon structure with the increasing number of repetition of the range, the number of repetition of each range may be properly determined such that a difference between the resistance of the carbon structure when the gas supply is stopped and the initial resistance before the gas supply is not large (for example, the difference is less than a preset threshold).

Meanwhile, as shown in FIGS. 5, 7 and 9, the shape and electrical properties of the carbon structure may be determined according to the type, intensity and/or duration of laser (for example, oscillator movement speed) in the carbonization of the carbide material by the method for manufacturing the gas sensor according to implementations.

Figure 17A:
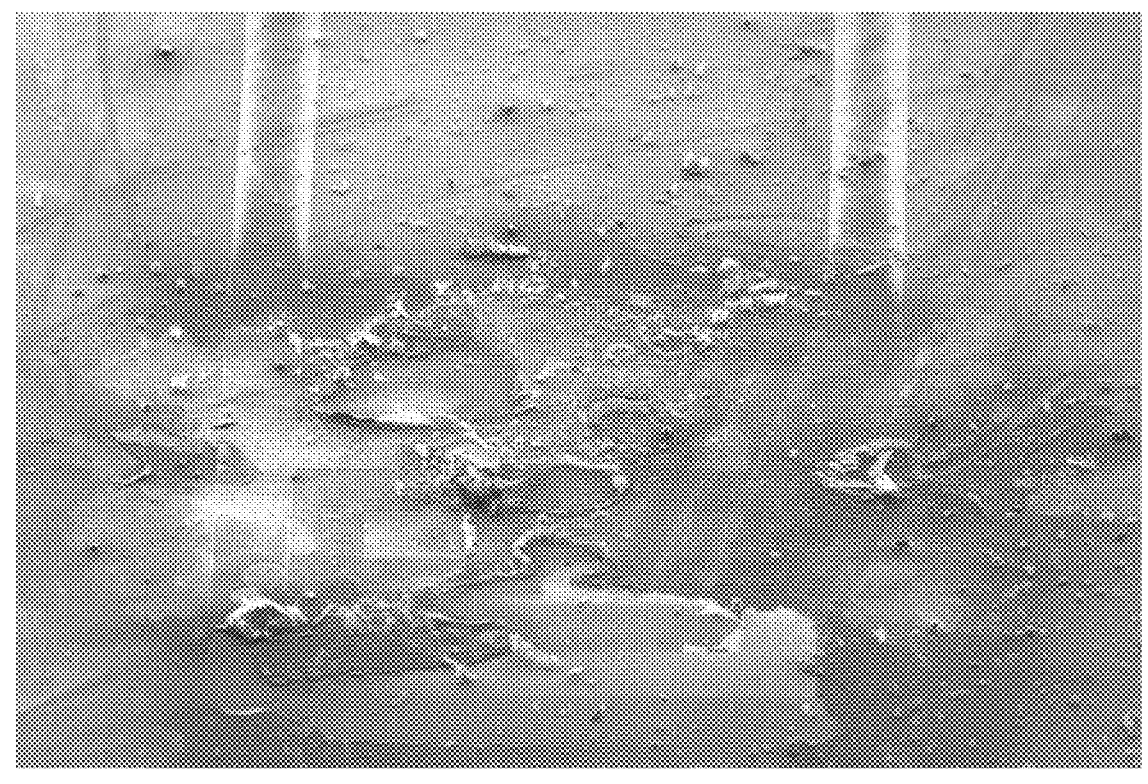
FIGS. 17A to 17C are examples of SEM images illustrating comparison of carbon structure formation results according to characteristics of laser.
Figure 17B:
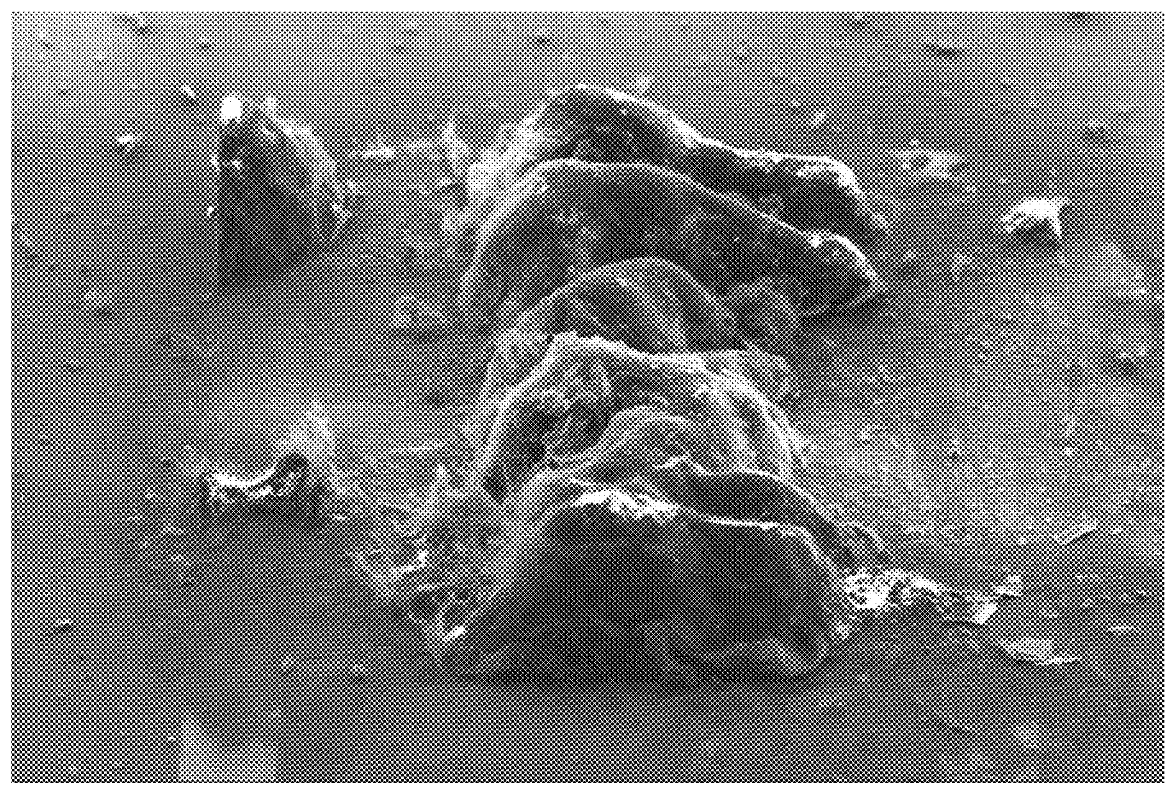
Figure 17C:
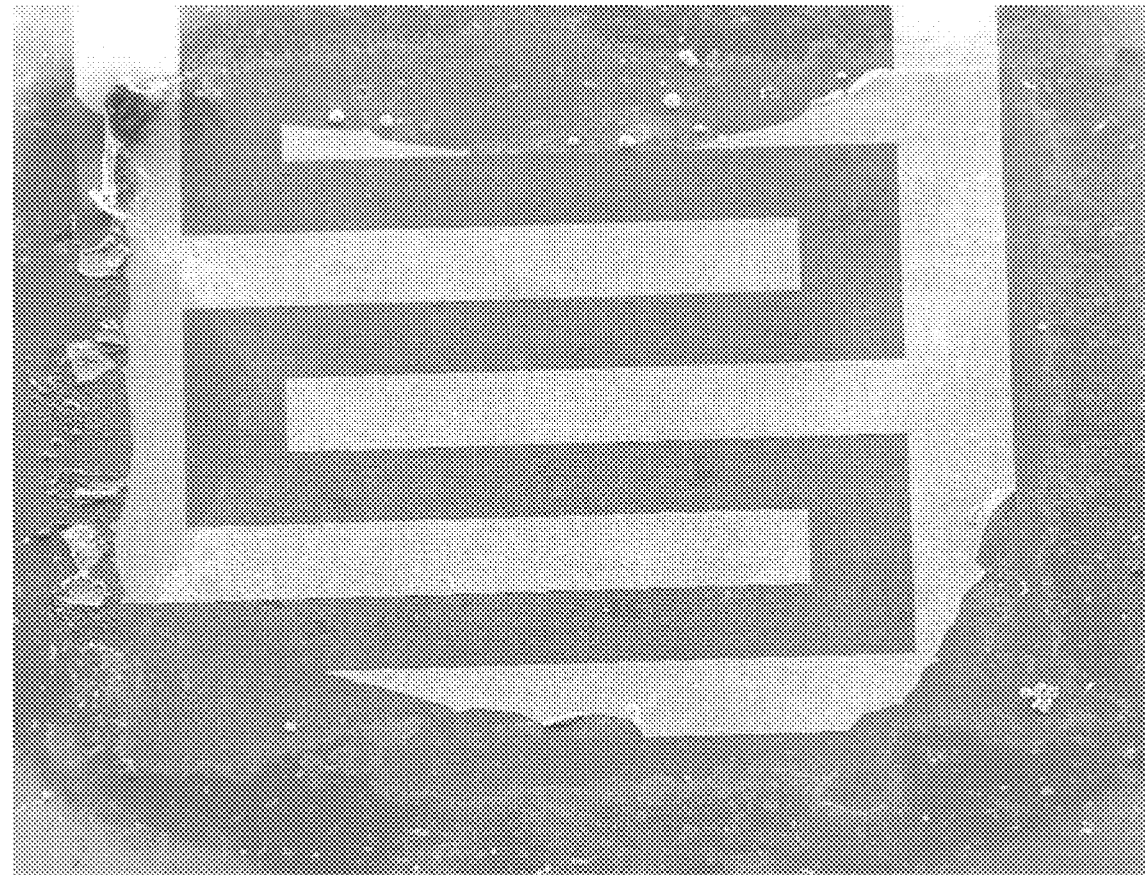

FIGS. 17A to 17C are examples of SEM images illustrating comparison of carbon structure formation results according to characteristics of laser.

FIG. 17A shows a result of the laser oscillator emitting the $CO_2$ laser to the SU-8 pattern 130 times while moving the laser oscillator at the speed of about 450 mm/sec with the output set to about 12 W. When the output of the laser oscillator and/or the number of laser irradiation is too large, as shown in FIG. 17A, SU-8 hardly remains on the substrate and the carbon structure is not formed.

On the other hand, FIG. 17B shows a result of the laser oscillator emitting the $CO_2$ laser to the SU-8 pattern 40 times while moving the laser oscillator at the speed of about 350 mm/sec with the output set to about 11.2 W. As shown, it is confirmed that at some areas, the carbon structure is formed by carbonization of SU-8, but due to very high movement speed of the laser oscillator, laser irradiation on SU-8 is not uniform, and in some areas illuminated with too much laser, SU-8 disappeared.

Additionally, FIG. 17C shows the carbon structure formed by increasing the experimental temperature in the process of manufacturing the gas sensor from 200° C. to 300° C. On the SEM image, the carbon structure is not seen and the underlying electrode structure is found, but carbon energy spectrum and oxygen energy spectrum analysis reveals that the carbon structure exists. As described above, the carbon structure may be formed in various planar or 3D arrangements, for example, a 2-dimensional thin film or a 3D vertical configuration, according to the process conditions in the process of preparing the carbon structure according to implementations.

Figure 18A:
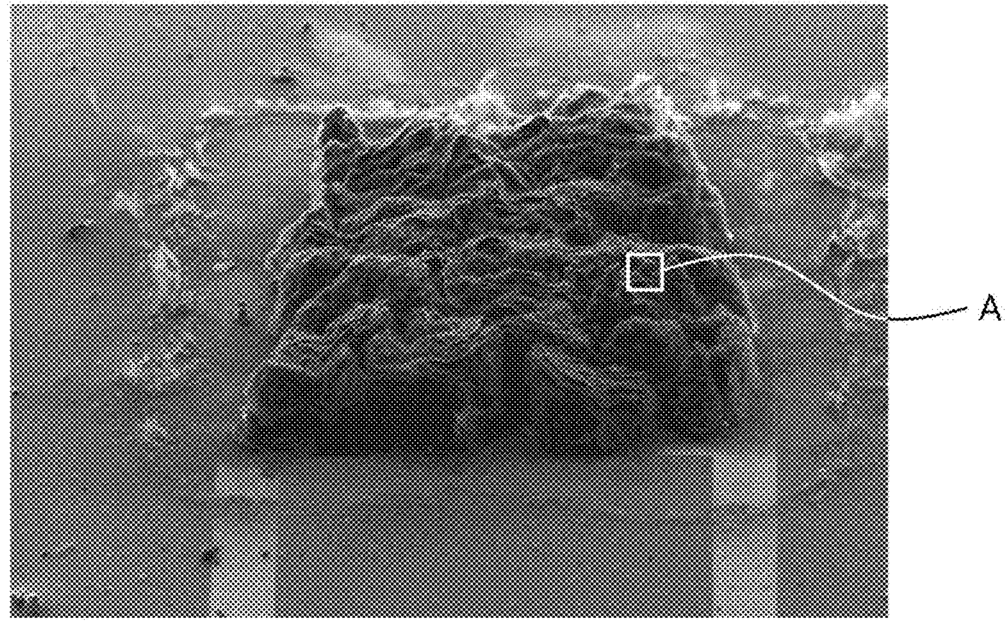
FIGS. 18A to 18C are examples of SEM images illustrating carbon structure formation results.

In contrast, FIG. 18A is an example of an SEM image illustrating the formation result of another carbon structure. This example shows a result of the laser oscillator emitting the $CO_2$ laser to the SU-8 pattern 30 times while moving the laser oscillator at about 200 mm/sec with the output set to about 10.4 W. Additionally, FIG. 18B is an enlarged image of section A in FIG. 18A, and FIG. 18C is an SEM image showing the side of the carbon structure shown in FIG. 18A.

Figure 18B:
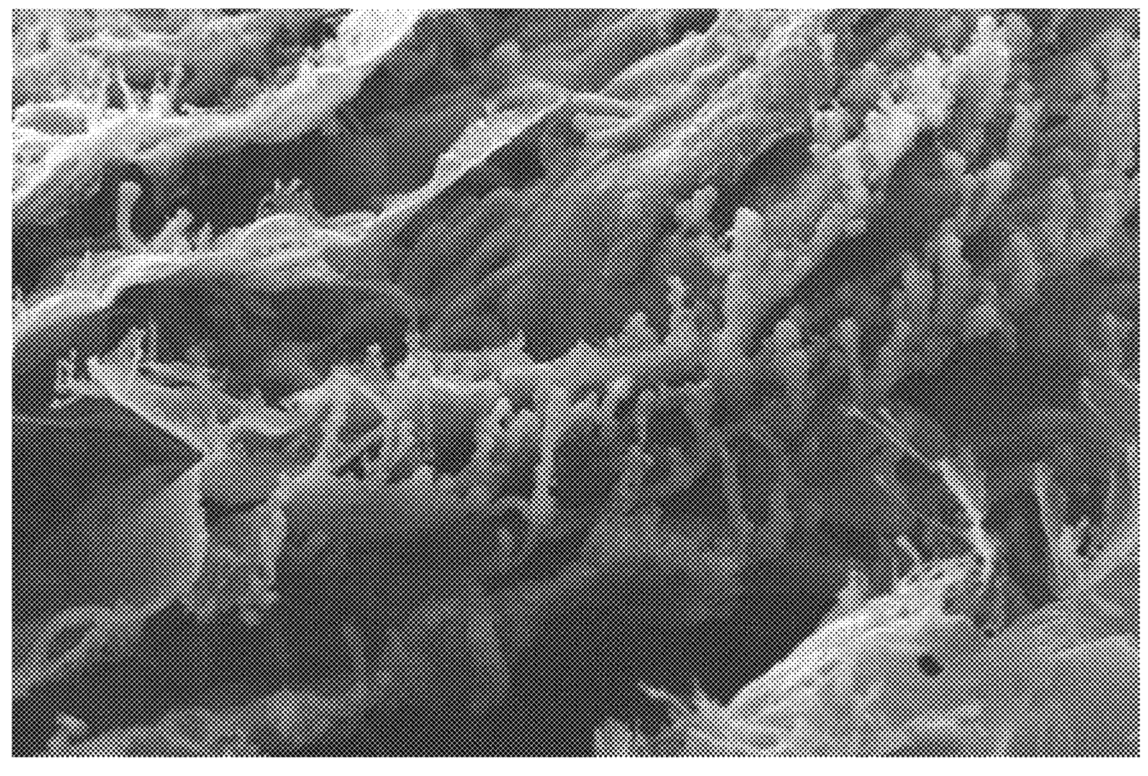
Figure 18C:
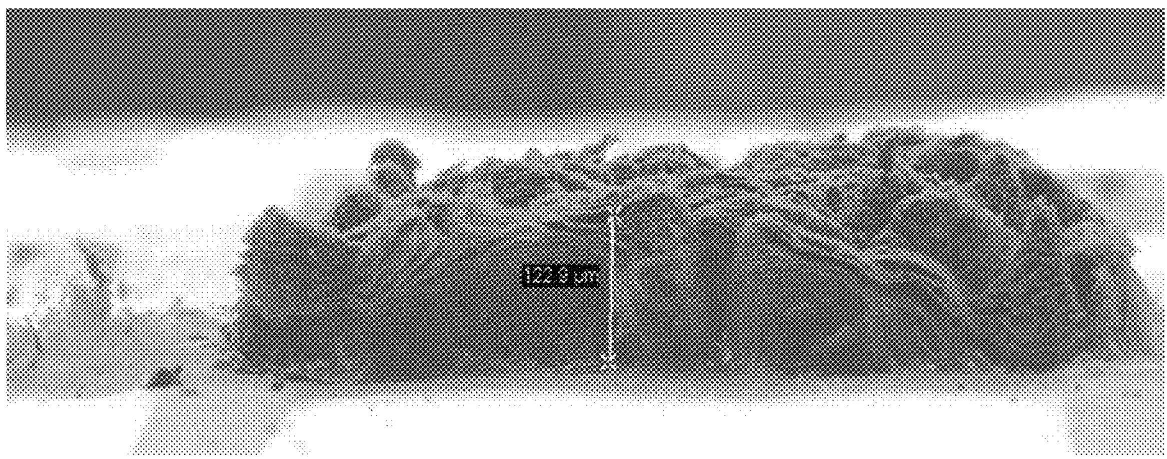

As shown, in the experiment shown in FIGS. 18A to 18C, compared to FIGS. 17A and 17B, the carbon structure conforming to the shape of the SU-8 pattern is formed by uniform laser irradiation on the SU-8 pattern. Accordingly, in the carbonization of the photoresist through the $CO_2$ laser, the output of the laser oscillator, the movement speed of the laser oscillator and/or the number of laser irradiation may be adjusted so that the carbon structure including the carbonized photoresist remains on the substrate.

The foregoing implementations of the present disclosure are illustrative, and a person having ordinary skill in the art to which the present disclosure pertains will appreciate that the implementations are easily modifiable into other specified forms without departing from the technical ideas or essential characteristics of the present disclosure. Therefore, the implementations described above should be understood as being illustrative in all aspects and not limiting. For example, respective components described as a combined form may be implemented in a discrete form, and similarly, the components described as a discrete form may also be implemented in a combined form.

The scope of the present disclosure is defined by the following claims than the detailed description, and should be construed as containing all changes or modifications derived from the meaning, scope, and equivalent of the claims.

What is claimed is:

1. A method for manufacturing a gas sensor, comprising:
forming an electrode pattern;
forming a carbide material layer on the electrode pattern;
carbonizing, based on an irradiation of a laser on the carbide material layer, the carbide material layer to form a carbon structure capable of adsorbing gas particles; and
electrically connecting a measurement device to the electrode pattern, wherein, based on the carbon structure being exposed to the gas particles, the measurement device is configured to measure electrical properties of the electrode pattern,
wherein the carbon structure is formed by carbonization of a material comprising carbon, the carbon structure comprising (i) a planar or 3-dimensional arrangement of at least one of a carbon compound, graphene, or graphene oxide, and (ii) pores configured to adsorb gas particles based on the planar or three-dimensional arrangement being imperfect,
wherein, based on the gas particles being adsorbed into the pores, electrical properties of the carbon structure change, and
wherein the measurement device is configured to measure the gas particles by measuring a change in the electrical properties of the electrode pattern caused by a change in the electrical properties of the carbon structure.

2. The method for manufacturing the gas sensor according to claim 1, wherein the carbide material layer comprises SU-8.

3. The method for manufacturing the gas sensor according to claim 1, wherein forming the carbon structure comprises, based on an irradiation of a carbon dioxide ($CO_2$) laser onto the carbide material layer, carbonizing the carbide material layer.

4. The method for manufacturing the gas sensor according to claim 3, wherein carbonizing the carbide material layer further comprises:
moving a laser oscillator configured to emit the $CO_2$ laser at a preset speed on the carbide material layer; and
adjusting at least one of the preset speed, an amount of the laser irradiation, or an output of the laser oscillator to thereby form the carbon structure having a planar or a 3-dimensional arrangement.

5. The method for manufacturing the gas sensor according to claim 1, wherein the carbide material layer comprises a photoresist, and
wherein forming the carbide material layer comprises mixing a photoresist solution with an ethanol solution and applying a mixed solution of the photoresist solution and the ethanol solution onto a substrate.

6. The method for manufacturing the gas sensor according to claim 5, wherein applying the mixed solution onto the substrate comprises adjusting a viscosity of the mixed solution of the photoresist solution and the ethanol solution to thereby form the carbide material layer with a preset thickness.

7. The method for manufacturing the gas sensor according to claim 5, wherein the ethanol solution comprises a bonding material that is dispersed in the ethanol solution and capable of selectively adsorbing the gas particles.

8. The method for manufacturing the gas sensor according to claim 1, further comprising:
after forming the carbon structure,
forming a bonding material layer capable of selectively adsorbing the gas particles on the carbon structure.

9. The method for manufacturing the gas sensor according to claim 8, wherein the forming of the bonding material layer comprises:
applying an ethanol solution in which quantum dots including a metal oxide are dispersed onto the carbon structure; and
evaporating the ethanol solution applied on the carbon structure.

10. A gas sensor, comprising:
an electrode pattern;
a carbon structure located on the electrode pattern, and having pores for adsorption of gas particles; and
a measurement device electrically connected to the electrode pattern, and configured to detect the gas particles based on (i) measurement of a change in electrical properties of the electrode pattern and (ii) the carbon structure being exposed to the gas particles,
wherein the carbon structure is formed by carbonization of a material comprising carbon, the carbon structure comprising (i) a planar or 3-dimensional arrangement of at least one of a carbon compound, graphene, or graphene oxide, and (ii) pores configured to adsorb gas particles based on the planar or three-dimensional arrangement being imperfect,
wherein, based on the gas particles being adsorbed into the pores, electrical properties of the carbon structure change, and
wherein the measurement device is configured to measure the gas particles by measuring the change in the electrical properties of the electrode pattern caused by a change in the electrical properties of the carbon structure.

11. The gas sensor according to claim 10, further comprising:
a bonding material layer located on the carbon structure and capable of selectively adsorbing the gas particles.

12. The gas sensor according to claim 11, wherein the bonding material layer comprises metal oxide quantum dots.

13. A method of operating a gas sensor, the method comprising:
exposing a carbon structure that is located on an electrode pattern and has pores for adsorption of gas particles to gaseous phase materials including the gas particles for a first preset time; and
measuring electrical properties of the electrode pattern after exposing to the gaseous phase materials,
wherein the carbon structure is formed by carbonization of a material comprising carbon, the carbon structure comprising (i) a planar or 3-dimensional arrangement of at least one of a carbon compound, graphene, or graphene oxide, and (ii) pores configured to adsorb gas particles based on the planar or three-dimensional arrangement being imperfect, and
wherein measuring the electrical properties of the electrode pattern comprises measuring a change in electrical properties of the electrode pattern caused by a change in electrical properties of the carbon structure.

14. The method according to claim 13, comprising:

interrupting a supply of the gaseous phase materials to the carbon structure for a second preset time to recover the electrical properties of the electrode pattern; and heating the carbon structure at a preset temperature.

15. The method according to claim 14, wherein exposing the carbon structure to the gaseous phase materials and interrupting the supply of the gaseous phase materials are repeatedly performed multiple times.

16. The method according to claim 14, further comprising:

adjusting at least one of the preset temperature, a length of the first preset time, or a length of the second preset time such that a difference between (i) the electrical properties of the electrode pattern after interrupting the supply of the gaseous phase materials and (ii) the electrical properties of the electrode pattern before exposing to the gaseous phase materials is less than a preset threshold.

* * * * *